United States Patent
Miller

(10) Patent No.: US 9,770,716 B2
(45) Date of Patent: Sep. 26, 2017

(54) MULTI-FLUIDIC CARTRIDGES FOR SAMPLE ANALYSIS AND METHODS FOR USING SAME

(71) Applicant: Abbott Point of Care Inc., Princeton, NY (US)

(72) Inventor: Cary James Miller, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 495 days.

(21) Appl. No.: 14/472,812

(22) Filed: Aug. 29, 2014

(65) Prior Publication Data

US 2014/0370583 A1    Dec. 18, 2014

Related U.S. Application Data

(63) Continuation of application No. 13/331,136, filed on Dec. 20, 2011, now Pat. No. 8,826,752.

(60) Provisional application No. 61/428,024, filed on Dec. 29, 2010.

(51) Int. Cl.
  *G01N 1/10* (2006.01)
  *B01L 3/00* (2006.01)
  *G01N 1/00* (2006.01)

(52) U.S. Cl.
  CPC ..... *B01L 3/50273* (2013.01); *B01L 3/502738* (2013.01); *G01N 1/10* (2013.01); *B01L 2200/16* (2013.01); *B01L 2300/0816* (2013.01); *B01L 2300/0867* (2013.01); *B01L 2400/0406* (2013.01); *B01L 2400/0481* (2013.01); *B01L 2400/0683* (2013.01); *B01L 2400/0688* (2013.01); *G01N 2001/002* (2013.01)

(58) Field of Classification Search
  None
  See application file for complete search history.

(56) References Cited

U.S. PATENT DOCUMENTS

| 3,756,920 A | 9/1973 | Kelbaugh et al. |
| 3,767,364 A | 10/1973 | Ritchie et al. |
| 3,796,544 A | 3/1974 | Zauft et al. |

(Continued)

FOREIGN PATENT DOCUMENTS

| CN | 1985167 | 6/2007 |
| DE | 102009001257 | 4/2010 |

OTHER PUBLICATIONS

U.S. Appl. No. 69/419,489, filed Dec. 3, 2010, Miller.
(Continued)

*Primary Examiner* — Robert R Raevis
(74) *Attorney, Agent, or Firm* — Kilpatrick Townsend & Stockton LLP

(57) ABSTRACT

The invention is directed to multi-fluidic cartridges for sample analysis and to methods of using said cartridges. In one embodiment, the cartridge comprises: (a) a first conduit beginning at a sample entry port for receiving a fluid sample and in fluid communication with one or more sensors; (b) a plurality of rupturable fluidic pouches, each containing a different fluid and in fluid communication with a respective delivery conduit configured for delivering a respective fluid to said first conduit; and (c) at least one pneumatic pump configured to move said fluid sample to said one or more sensors and for transporting at least one of said different fluids to said first conduit.

15 Claims, 14 Drawing Sheets

(56) References Cited

U.S. PATENT DOCUMENTS

| | | | |
|---|---|---|---|
| 4,052,161 | A | 10/1977 | Atwood et al. |
| 4,649,028 | A | 3/1987 | Kaltenbach et al. |
| 4,929,426 | A | 5/1990 | Bodai et al. |
| 4,994,167 | A | 2/1991 | Shults et al. |
| 5,037,614 | A | 8/1991 | Makita et al. |
| 5,096,669 | A | 3/1992 | Lauks et al. |
| 5,112,455 | A | 5/1992 | Cozzette et al. |
| 5,134,079 | A * | 7/1992 | Cusack .................. G01N 35/08 422/81 |
| 5,200,051 | A | 4/1993 | Cozzette et al. |
| 5,212,050 | A | 5/1993 | Mier et al. |
| 5,316,727 | A | 5/1994 | Suzuki et al. |
| 5,405,510 | A | 4/1995 | Betts et al. |
| 5,447,440 | A | 9/1995 | Davis et al. |
| 5,863,502 | A | 1/1999 | Southgate et al. |
| 5,873,990 | A | 2/1999 | Wojciechowski et al. |
| 6,222,371 | B1 | 4/2001 | Snyder |
| 6,319,410 | B1 | 11/2001 | Allington et al. |
| 7,041,206 | B2 | 5/2006 | Gephart et al. |
| 7,419,821 | B2 | 9/2008 | Davis et al. |
| 7,547,557 | B2 | 6/2009 | LaBorde et al. |
| 7,682,833 | B2 | 3/2010 | Miller et al. |
| 8,007,999 | B2 | 8/2011 | Holmes et al. |
| 8,669,047 | B2 | 3/2014 | Holmes et al. |
| 2003/0170881 | A1 | 9/2003 | Davis et al. |
| 2005/0054078 | A1 | 3/2005 | Miller et al. |
| 2005/0148091 | A1 | 7/2005 | Kitaguchi et al. |
| 2005/0153430 | A1 | 7/2005 | Ohtaka |
| 2007/0144277 | A1 | 6/2007 | Padmanabhan et al. |
| 2007/0264629 | A1 | 11/2007 | Holmes et al. |
| 2012/0142025 | A1 | 6/2012 | Miller |
| 2012/0167672 | A1 | 7/2012 | Miller |
| 2012/0168305 | A1 | 7/2012 | Hunter |
| 2014/0193806 | A1 | 7/2014 | Holmes et al. |

OTHER PUBLICATIONS

U.S. Appl. No. 61/419,485, filed Dec. 3, 2010, Miller.
U.S. Appl. No. 61/288,189, filed Dec. 18, 2009, Doyle, et al.
Office Action for Chinese Appl. No. 201180063234.5 dated Aug. 15, 2014.
International Search Report and Written Opinion for PCT/US2011/066048 mailed May 21, 2012.
i-STAT System Manual (2010).
i-STAT 1 System Manual (2011), pp. 1-612.
i-STAT PCA System Manual (2011), pp. 1-466.

* cited by examiner

MULTI-FLUIDIC CARTRIDGES FOR SAMPLE ANALYSIS AND METHODS FOR USING SAME

CROSS-REFERENCE TO RELATED APPLICATIONS

This is a continuation of U.S. patent application Ser. No. 13/331,136, filed Dec. 20, 2011, which claims priority to U.S. Provisional Application No. 61/428,024, filed Dec. 29, 2010, the entire contents and disclosures of which are hereby incorporated by reference.

FIELD OF THE INVENTION

The present invention relates to devices for use in medical testing and analysis. More particularly, the present invention relates to multi-fluidic disposable cartridges for fluidic analysis, especially for blood analysis, and to reader devices for such cartridges.

BACKGROUND OF THE INVENTION

With the continued advancement of medical technology and of portable electronics and mechanics, handheld diagnostic equipment for a multitude of types of tests on biological samples has become available.

Laboratory tests on biological samples have traditionally been performed for diagnosis, screening, disease staging, forensic analysis, pregnancy testing, drug testing, and other reasons. While a few qualitative tests, such as pregnancy tests, have been reduced to simple kits for the patient's home use, a large number of quantitative tests still require elaborate procedures that often necessitate the expertise of trained technicians in a laboratory setting using sophisticated instruments. In recent years, some of these tests have been made available to medical practitioners and the like for in situ analysis by using handheld testing devices that embody sensors and computational electronics for sample analysis, and mechanical actuation assemblies for manual and/or automated sample and testing fluid manipulation. Such handheld testing devices provide the advantage of being able to perform analysis and testing at the point of care for immediate results that could improve diagnostic timeliness and accuracy.

U.S. Pat. No. 6,222,371 by Snyder, for example, describes a handheld boiler and coolant fluid testing apparatus with test fluid reservoirs in the testing apparatus for receiving fluids to be tested. The described apparatus includes a main fluid reservoir and an overflow reservoir, with means for controlling fluid levels for improved testing accuracy and consistency.

For testing of biological samples, testing devices with disposable sample repositories have been used. U.S. Pat. No. 4,929,426 by Bodai et al., U.S. Pat. No. 4,994,167 by Shults et al., and U.S. Pat. No. 5,405,510 by Betts et al. describe portable biological fluid measuring devices with detachable and disposable sample cartridges. Bodai et al. describe a pH testing apparatus that houses internal blood sample holding cartridges for receiving blood samples deposited into the apparatus using a syringe. Shults et al. describe a testing device with a detachable cartridge that includes a membrane for receiving a fluid sample, the membrane being maintained in contact with electrodes of the testing device for testing the fluid sample. Betts et al. describe an analyte measuring device with a mated disposable cartridge that includes an inlet for introduction of fluids, sensors for performing the tests, and an electronic connection for providing testing controls and for communicating results to the measuring device.

Additionally, single use discrete sample carriers, and corresponding testing devices, have been developed for separate sample collection and for providing a simple interface to present collected samples to the testing device.

U.S. Pat. No. 5,037,614 by Makita et al., U.S. Pat. No. 5,316,727 by Suzuki et al., and U.S. Pat. No. 7,547,557 by LaBorde et al. describe discrete sample carriers for collecting test samples and presenting the collected samples to a corresponding testing device. Makita et al. describe using a test paper stick for collecting a blood sample, and inserting the test paper stick into an opening of a testing device for performing optical tests on the blood sample collected on the test paper. Suzuki et al. describe an enclosed test piece internally embodying the test paper, the test piece having an opening for collecting a blood sample onto the test paper and another opening for allowing optical testing when inserted in a corresponding testing device. LaBorde et al. describe a sample carrier embodying a sample receiving port and flow structure from the receiving port to an open test strip for allowing testing by a magnetic reader device.

Correspondingly, U.S. Pat. No. 5,096,669 by Lauks et al. describes a handheld sensing device for measuring analytes in a blood sample. Other handheld devices are described in U.S. Pat. No. 5,873,990 by Wojciechowski et al., U.S. Pat. No. 7,041,206 by Gephart et al. Lauks et al., Wojiechowski et al., and Gephart et al. describe single use test cartridges as fluid sample carriers for insertion into a handheld test apparatus for performing different types of tests on the fluid samples. In particular, Lauks et al. describe an apparatus and cartridge system commercially known as the i-STAT® point-of-care blood testing system, which uses disposable cartridges with sensors for performing one or more blood tests. These cartridges are operated using a portable analyzer which has a display for providing test results and other information to the user. The i-STAT® system is described in detail by the i-STAT® System Manual (2010) (Abbott Point of Care Inc., Princeton, N.J.), which is incorporated here in its entirety.

U.S. Pat. No. 7,419,821 by Davis et al. describes in detail a sample-carrying cartridge used for the i-STAT® system. Such cartridges include an inlet for receiving a sample, separate repositories for the sample and a testing liquid, and channeling mechanisms for mixing the liquids. The apparatus for use with this cartridge includes a mechanical actuator that triggers the mixing by applying mechanical force to an appropriate portion of the test cartridge.

With the continued advancement of cartridge design for accommodating increasingly sophisticated tests, there has been a need for parallel advancement in reading devices for actuating increasingly complex testing cartridges. To meet the needs for such tests, sensor and computational electronics and mechanical actuation elements have needed to become more elaborate.

SUMMARY OF THE INVENTION

The present invention is directed to multi-fluidic cartridges for sample analysis, preferably suitable for point-of-care testing, and to methods for using such cartridges. In one embodiment, the invention is directed to a multi-fluidic cartridge for sample analysis, comprising: (a) a first conduit beginning at a sample entry port for receiving a fluid sample and in fluid communication with one or more sensors; (b) a plurality of rupturable fluidic pouches, each containing a different fluid and in fluid communication with a respective delivery conduit configured for delivering a respective fluid to the first conduit; and (c) at least one pneumatic pump configured to move the fluid sample to the one or more sensors and for transporting at least one of the different fluids to the first conduit. Each different fluid optionally is selected from the group consisting of a reagent fluid, a wash fluid, a calibrant fluid, and a diluent, among others.

In another embodiment, the invention is directed to a process for analyzing a fluid sample with a multi-fluidic cartridge, comprising the steps of: (a) introducing the fluid sample into a sample entry port and allowing the fluid sample to enter a first conduit beginning at the sample entry port and in fluid communication with one or more sensors; (b) rupturing a plurality of fluidic pouches, each containing a different fluid and in fluid communication with a respective delivery conduit configured for delivering the fluid to the first conduit; (c) transporting the different fluids through the delivery conduits and to the first conduit; (d) transporting the fluid sample through the first conduit and over the one or more sensors; and (e) analyzing the fluid sample at the one or more sensors for the presence or concentration of an analyte or a property of the fluid sample. The process optionally includes a step of mixing at least one of the different fluids with the fluid sample in the first conduit. Optionally, at least one of the different fluids is transported to the first conduit before step (d), and at least one of the different fluids is transported to the first conduit after step (d).

The first conduit preferably includes a capillary stop oriented between the sample entry port and the one or more sensors. Operation of a pump, for example, may cause the fluid sample to pass through the capillary stop and to the one or more sensors.

In a preferred embodiment, at least two of the delivery conduits are in fluid communication with a shared conduit configured for delivering a plurality of fluids from the at least two of the delivery conduits to the first conduit. The shared conduit may be in fluid communication with the first conduit at a point upstream or downstream of the capillary stop. Preferably, the first conduit ends in a waste chamber. Thus, the processes of the invention optionally include a step of transporting a plurality of the different fluids from at least two of the delivery conduits through the shared conduit and to the first conduit.

The cartridge may include a single pneumatic pump that controls movement of the fluid sample and the plurality of different fluids, or alternatively, a plurality of pneumatic pumps, one of which, for example, controls movement of the fluid sample, and at least one of which controls movement of the plurality of different fluids. In one aspect, the cartridge includes a plurality of pneumatic pumps, and movement of each of the different fluids is controlled by a different pneumatic pump.

In one embodiment, the plurality of fluidic pouches includes a first fluidic pouch and a second fluidic pouch, wherein the first fluidic pouch contains a first fluid, optionally a diluent, and a first pneumatic pump controls movement of the first fluid to the first conduit and controls movement of the fluid sample in the first conduit, and wherein the second fluidic pouch contains a second fluid, movement of which is controlled by a second pneumatic pump.

Other features and advantages of the invention will become apparent from the following detailed description, taken in conjunction with the accompanying figures, which illuminate, by way of example, various features of embodiments of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying figures.

DETAILED DESCRIPTION OF THE PREFERRED EMBODIMENTS

The present invention relates to multi-fluidic disposable assay cartridges and to reader devices and actuation mechanisms for manipulating such cartridges. By "multi-fluidic" it is meant that the cartridges include two or more fluid-containing pouches for separately providing two or more fluids, such as one or more reagent fluids, wash fluids, calibrant fluids, diluents, and the like, for use in sample analysis. In preferred embodiments, the reader and associated actuation mechanism are configured such that they can independently rupture the two or more fluid-containing pouches in a predetermined manner causing the controlled release of fluids therefrom, and effectuating improved sample analysis.

Figure 21:
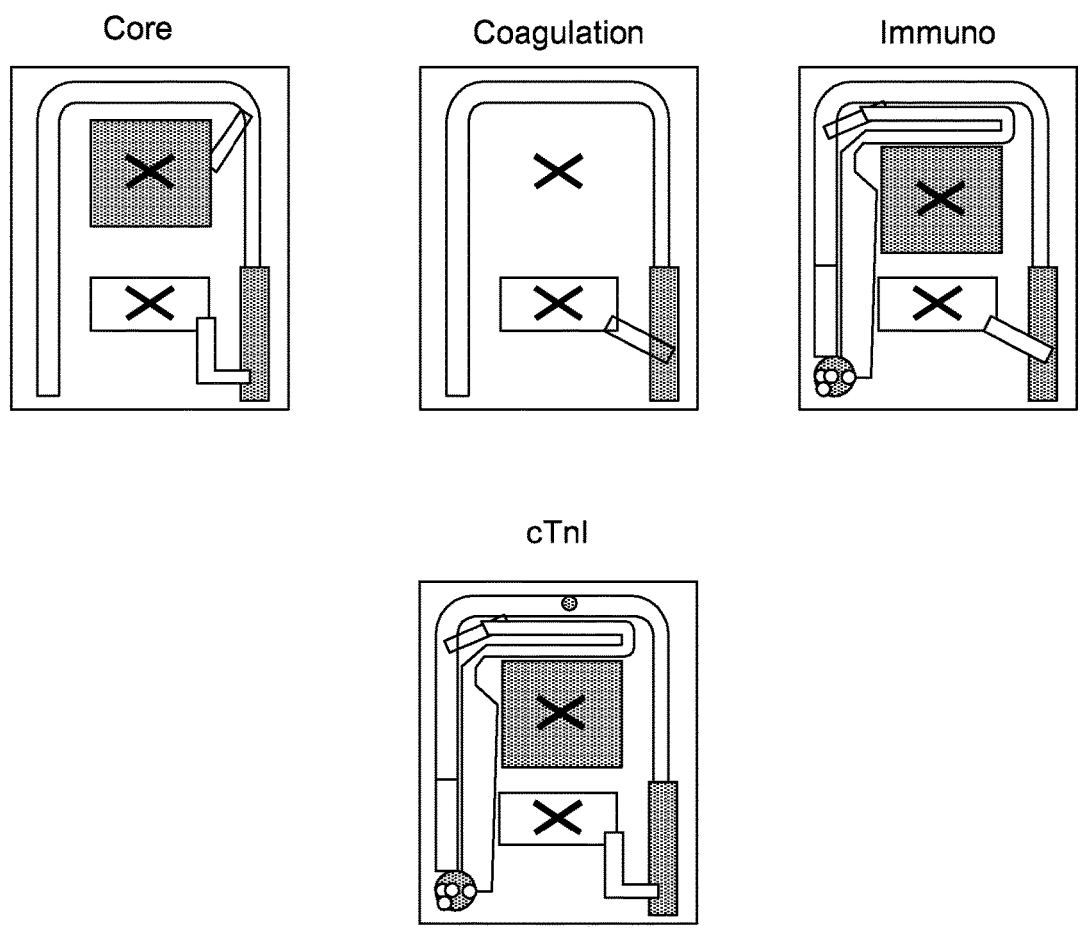
FIG. 21 illustrates several i-Stat® system legacy cartridge designs.

The cartridges and readers preferably are based on the i-STAT® point-of-care blood testing system, which uses disposable cartridges having sensors for performing one or more blood tests. These cartridges are operated using a portable reader that has a display for providing test results and other information to the user. The i-STAT® system is described in detail by the i-STAT® System Manual (2010) (Abbott Point of Care Inc., East Windsor, N.J.), which is incorporated here in its entirety. One skilled in the art will recognize that the disclosed mechanisms can be adapted to other blood testing systems, both those used at the point-of-care and in central laboratories. It is also understood that the disclosed mechanisms can be adapted to other handheld analyzers or combination testing cartridges and portable clinical analyzers, including, but not limited to, those having advanced bioscience technology, and including those which are available or may become available. Currently available i-STAT® systems, as shown in FIG. 21, have been limited to mono-fluidic cartridges, such as cTnI analysis cartridges, that employ a single liquid reagent, e.g., calibrant or wash fluid, and to cartridges that do not include any liquid reagents, e.g., the coagulation analysis cartridge.

Conventional mono-fluidic cartridges typically have two actuation points for actuation when inserted into a reader. The first actuation point is for rupturing the single fluid pouch, and the second actuation point is for actuating a pumping mechanism for moving various fluids within the cartridge. The cartridges of the present invention, in contrast, may beneficially include multiple fluidic components, and typically involve more than two actuation points for actuation when inserted into a reader.

Multi-Fluidic Cartridges

The orientation and configuration of multi-fluidic cartridges of the present invention may vary widely. In one embodiment, the cartridge comprises: (a) a first conduit beginning at a sample entry port for receiving a fluid sample and in fluid communication with one or more sensors; (b) a plurality of rupturable fluidic pouches, each containing a different fluid and in fluid communication with a respective delivery conduit configured for delivering a respective fluid to the first conduit; and (c) at least one pneumatic pump configured to move the fluid sample to the one or more sensors and for transporting at least one of the different fluids to the first conduit. As used herein, the "first conduit" refers to a conduit beginning with a sample entry orifice for introduction of a fluid sample and including a sensing region that includes one or more electrodes for sample analysis. The first conduit preferably terminates in a waste chamber for receiving excess or used fluids that are used in the testing process. In a preferred embodiment, at least two of the delivery conduits are in fluid communication with a shared conduit configured for delivering a plurality of fluids from at least two of the delivery conduits to the first conduit.

The plurality of fluidic cartridges may be oriented longitudinally, longitudinally or both laterally and longitudinally, with respect to one another. As used herein, "longitudinal" means a direction parallel to a direction of insertion of the cartridge into the cartridge reader, and "lateral" means a direction parallel to the width of the cartridge.

Figure 1:
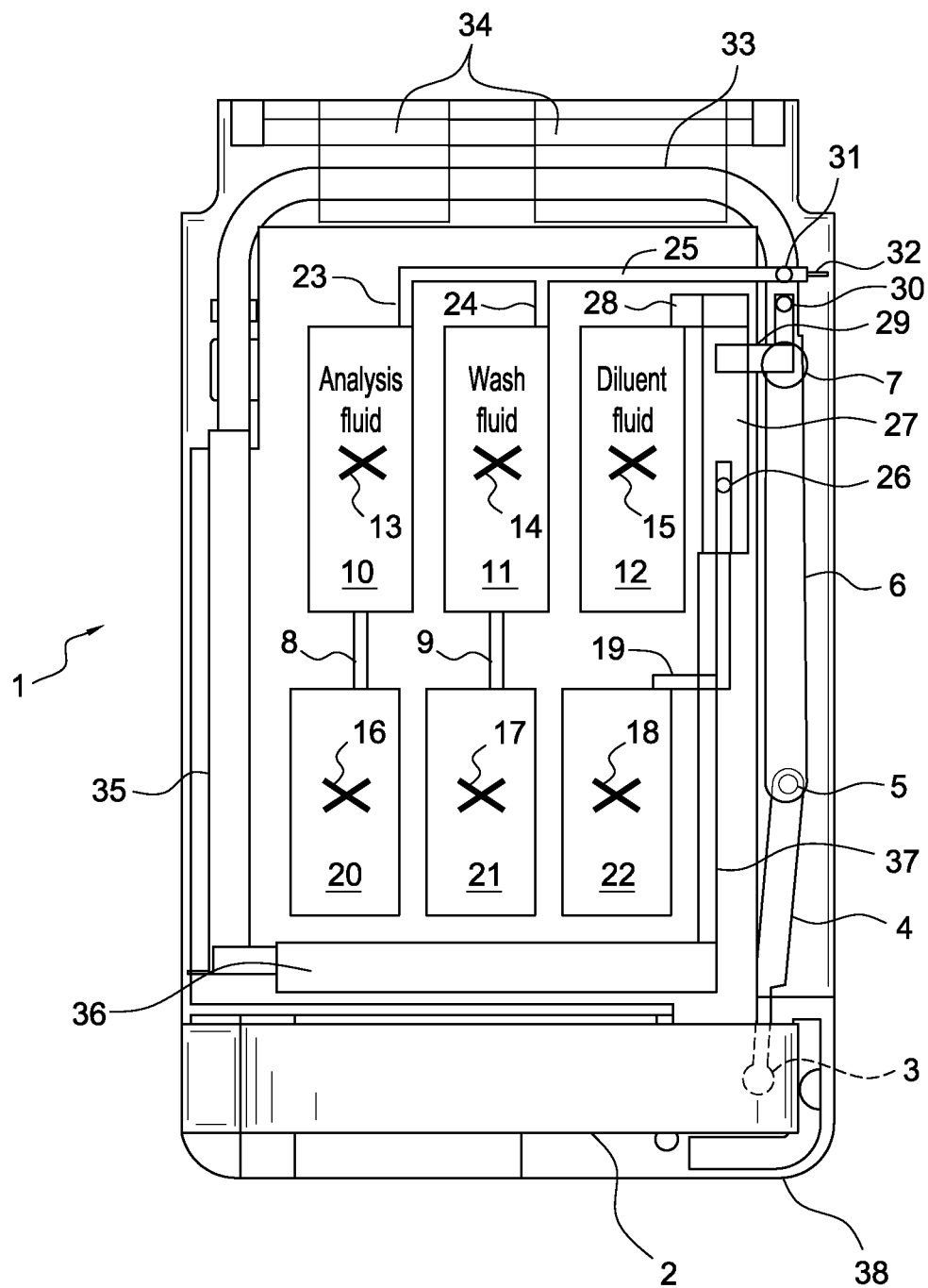
FIG. 1 illustrates an exemplary multi-fluidic cartridge according to one embodiment of the invention.

One non-limiting embodiment of a multi-fluidic cartridge 1 according to the present invention is shown in FIG. 1. As shown, the cartridge 1 comprises a cartridge housing 38, which defines a series of conduits and cavities. The housing 38 preferably is formed of a rigid material such as plastic and may be formed in multiple sections. For example, the housing may be formed from a cover section and a base section and may include a tape or adhesive sheet therebetween for separating conduits in the cover and base sections as well as providing a membrane for one or more pumping elements, as described in U.S. Pat. No. 5,096,669. In another embodiment, the housing may be formed from a single molded plastic piece having a cover portion and an opposing base portion that are foldable about a hinge region, such that the cover and base portions may be secured to one another after being folded together, as described in U.S. Provisional Patent Appl. No. 61/288,189, the entirety of which is incorporated herein by reference.

The cartridge housing 38 includes a sample entry port 3, in which a sample, e.g., blood, may be introduced. Once introduced, the sample entry port 3 is covered by a sliding closure member 2. As shown, the closure member 2 is in a closed position and covers sample entry port 3. An exemplary closure member is described in jointly-owned U.S. Pat. No. 7,682,833, the entirety of which is incorporated herein by reference. Upon introduction into the sample entry port, capillary action pulls the sample into holding chamber 4. As shown, the holding chamber 4 extends from the base section, through a hole 5 in the tape that is between the base section and the cover section, and into conduit 6 in the cover section. In other embodiments, not shown, the holding chamber is oriented exclusively in either the base section or the cover section. In the embodiment shown, capillary action preferably pulls the sample distally through conduit 6 to optional sample extraction unit 7, which absorbs a portion of the sample to facilitate high range sample dilution, as described in U.S. Provisional Patent Appl. No. 61/419,489, entitled "Sample Metering Device and Assay Device with Integrated Sample Dilution," the entirety of which is incorporated herein by reference. In essence, in the aspect shown, a small volume of sample is absorbed within the sample extraction unit 7, and in subsequent process steps a diluent from one or more of the multiple fluidic pouches is pumped such that it passes over and/or through the sample extraction unit 7 via dilution conduit 29 and extracts a metered portion of the sample therefrom, preferably for high range sample dilution, e.g., dilutions on the order of from about 50:1 to 50,000:1, from 100:1 to 1,000:1 or from 5,000:1 to 25,000:1. The resulting diluted sample is pumped through opening 30, which optionally comprises a capillary stop, to an analysis area comprising one or more electrodes 34.

In another aspect, not shown in FIG. 1, the device may be configured for low range sample dilution, e.g., sample dilutions or mixtures that are less than about 50:1 (v/v diluent:sample), less than 25:1, less than 10:1 or less than 5:1, as described in U.S. Provisional Application No. 61/419,485, entitled "Sample Metering Device and Assay Device with Integrated Sample Dilution," the entirety of which is incorporated herein by reference. In this aspect, the device preferably does not include a sample extraction unit and the diluent mixes with a metered sample to form a low range diluted sample that is transported through the capillary stop and to one or more sensors for sample analysis. One configuration for implementing a low range sample dilution is discussed further below in connection with FIG. 2H.

It should be noted that the multi-fluid concepts of the present invention may or may not include a dilution feature.

As a result, the feature that stops initial motion of the sample fluid after it is introduced into the cartridge, e.g., the sample extraction unit or capillary stop, may be oriented upstream or downstream of the conduit that transfers fluids from the multiple fluid pouches to the first conduit.

The cartridge housing, preferably the base section of the cartridge housing, also has a plurality of cavities for housing a plurality of fluid-containing pouches. In the embodiment shown in FIG. 1, the cartridge comprises three cavities 10, 11, 12 for housing three fluid-containing pouches. In other embodiments, the cartridge may comprise two, three, four, five or more cavities for housing a corresponding number of fluid-containing pouches. As discussed in greater detail below, each cavity preferably includes a pin at the bottom thereof and optionally a hinged disc at the top of the cavity, preferably formed by the cover section of the cartridge. Upon or after insertion of the cartridge in the reader device, pressure may be applied to one or more of the hinged discs in the region of actuation points 13, 14 and/or 15, preferably in a predetermined order, causing each disc to flex inwardly upon the associated pouch contained in the associated cavity and causing it to rupture on a pin and release the fluid contained therein. Each cavity has an associated conduit 23, 24 and 28 for receiving fluid from the corresponding ruptured pouch or associated cavity. In the embodiment shown, fluid from first pouch 10 is transferred, optionally by capillary action, into conduit 23 and conduit 25; fluid from second pouch 11 is transferred, optionally by capillary action, into conduit 24 and conduit 25; and fluid from third pouch 12 (which preferably comprises a diluent) is transferred, optionally by capillary action, into conduit 28 and conduit 27 (preferably a diluent conduit).

The order and timing of rupturing of the first, second and third (or more) pouches may vary widely depending on the test being employed as well as the type of fluids contained in the respective pouches. In one embodiment, for example, the first pouch comprises an analysis fluid, the second pouch comprises a wash fluid and the third pouch comprises a diluent fluid. In one embodiment, the diluent pouch is ruptured first and a portion of the fluid is used to dilute the sample and deliver the mixture to the sensor area. Second, the wash fluid pouch is ruptured and fluid is delivered to the sensor area to wash the sensor. Lastly, the analysis fluid pouch is ruptured and fluid is delivered to the sensor area. This fluid contains a reagent that interacts with the sensor to generate a signal that relates to the target analyte in the sample. Other sequences will be apparent to those skilled in the art, e.g., where wash and analysis fluids are combined in a single pouch. Another alternative, e.g., for a sequential sandwich immunoassay where analyte capture to a first antibody precedes exposure to the second signal antibody operates as follows: a first pouch with wash fluid to remove unbound analyte in a sample, a second pouch with a signal antibody, a third pouch with a second wash fluid and a fourth pouch with the analysis fluid.

In the embodiment shown, each pouch (and pouch cavity) has a corresponding pump associated therewith, although this is an optional feature. Each of the first, second and third pumps may be activated upon or after (in a predetermined or preprogrammed sequence) insertion into a reader, preferably independently from one another, by first, second and third plungers, respectively, within the reader. The plungers preferably contact the first, second and third pumps, respectively, at first actuation point 16, second actuation point 17 and third actuation point 18. First pump 20 is configured to pump air through conduit 8 to pouch 10 (or associated cavity) in order to pump fluid through conduits 23 and 25, through hole 31 (optionally a capillary stop) and into analysis conduit 33. Second pump 21 is configured to pump air through conduit 9 to pouch 11 (or associated cavity) in order to pump fluid through conduits 24 and 25 through hole 31 (optionally a capillary stop) and into analysis conduit 33. Third pouch 12 preferably is configured to be suitable for sample dilution and as a result has a different flow path than fluid from the first pouch 10 and the second pouch 11. In embodiments with separate pumps, the main purpose of the actuators of the pouches is to rupture each associated pouch, freeing the fluid to flow under the control of the respective pumps.

In the embodiment shown, after third pouch 12 is ruptured, fluid, e.g., diluent, contained therein flows through conduit 28 and into conduit 27 (referred to as a diluent conduit when the third fluid comprises diluent). Excess fluid may be transferred via waste conduit 37 to waste chamber 36. In a subsequent process step, third pump 22 is configured to pump air through conduit 19, through orifice 26 (optionally a capillary stop), and into diluent conduit 27 causing fluid contained therein to pass through conduit 29 and into contact with sample extraction unit 7. In this aspect, the fluid in conduit 28 preferably flows through and/or over extraction unit 7 such that a portion of the sample is extracted from the sample extraction unit and into the fluid. Continued pumping action of third pump 22 causes the fluid and extracted sample (preferably in the form of a "diluted sample") to pass through opening 30 and into analysis conduit 33. The sample then passes over the analysis area comprising electrodes 34 for assay formation and analyte detection. Fluid from the first, second and third pouches that has been transferred over analysis conduit 33, e.g., as a reactant or wash fluid, may be pumped via conduit 35 to waste chamber 36 when desired.

In an analogous embodiment, not shown, the diluent pouch is omitted, as is the dilution feature, and here sample, wash fluid and analysis fluid each pass directly into conduit 33 via shared conduit 25. See FIG. 2A, discussed below. This design may be adopted, for example, when the assay requires no sample dilution step.

Figure 2A:
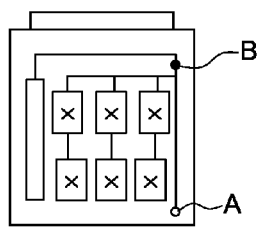
FIGS. 2A-2I illustrate additional exemplary multi-fluidic cartridges according to other embodiments of the invention.

FIGS. 2A-2I illustrate schematically various optional configurations for multi-fluidic cartridges according to other embodiments of the invention. In the figures, the sample entry port is designated "A" and a fluid stop, e.g., capillary stop or other fluid flow stopping feature, is designated "B." FIGS. 2A-2I also illustrate actuation points (at each "x") for additional testing features, such as multipoint calibration for core testing, wash and analysis for immunoassays, and the like. FIG. 2A illustrates an embodiment comprising three fluid pouches, each containing a respective pump. The fluid from the three pouches may be directed, preferably independently, through a single shared conduit to a region between the sample entry port A and the fluid stop B, and optionally mixed with the fluid sample disposed therebetween. In some embodiments, the single shared conduit intersects with the first conduit upstream of the stopping feature, while in other embodiments the single shared conduit intersects the first conduit downstream of the stopping feature. In another aspect, one or more fluid conduits (optionally shared conduits) join the first conduit upstream of the stopping feature and one or more other fluid conduits (optionally shared conduits) join the first conduit downstream thereof. As shown in FIG. 2A, the testing cartridge may include chambers and corresponding actuation points aligned in rows of three.

Figure 2B:
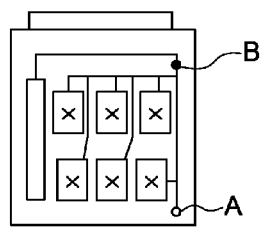

FIG. 2B illustrates an embodiment comprising multiple fluid-containing pouches, here, six fluid-containing pouches, which may be individually ruptured as discussed above. The individual fluids may, for example, be reagents, wash fluids, diluents, or air. The manifold allows a digital train of fluid/air segments to be generated and pumped along the outer sensor/waste conduit. Reagents optionally may be pumped into each other to form a new combined reagent (which may, for example, have been unstable if premixed in one of the pouches.) In this embodiment, at least one of the pouches (such as the lower right pouch) preferably is filled with air and is plumbed to move the sample from the inlet and into the analysis area.

Figure 2C:
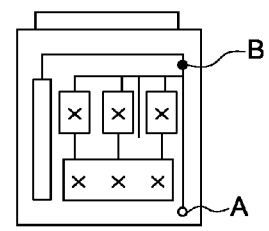
Figure 2D:
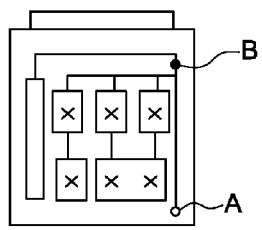
Figure 2E:
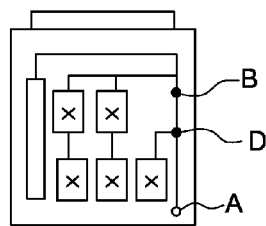
Figure 2F:
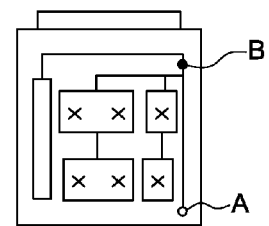
Figure 2G:
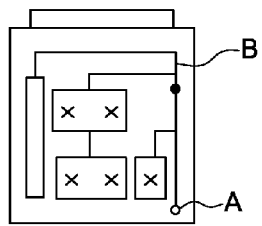

FIG. 2C illustrates a single pump controlling the simultaneous output of fluid from three different fluid pouches. FIG. 2D illustrates an embodiment where a single pump controls the (simultaneous) output of fluid from multiple (two) pouches. Specifically, FIG. 2D shows a single pump controlling fluid flow from the second and third pouches and a separate pump for controlling fluid flow from the first pouch. FIG. 2E illustrates an embodiment employing two fluid pouches, each having its own respective pump, and a third pump configured to control movement of a metered sample, which is formed between pump opening D and fluid stop B. FIG. 2F shows an embodiment comprising two fluid pouches, each having its own respective pump, and wherein the first pouch is larger than the second pouch and holds a larger volume of fluid than the second pouch. FIG. 2G illustrates an embodiment comprising a single fluid pouch and two pumps, wherein the first pump is configured to move fluid from the single fluid pouch, and the second pump is configured to control movement of a metered sample, which is formed between the pump opening and the capillary stop, as described above in FIG. 2E.

Figure 2H:
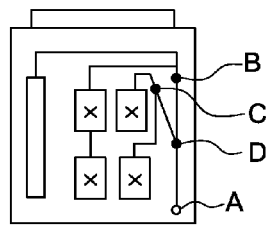

FIG. 2H illustrates an embodiment that is suited for low range sample dilution or sample mixing as discussed above, e.g., sample dilutions or mixtures that are less than about 50:1 (v/v diluent:sample). In this embodiment, sample is introduced into the cartridge and preferably flows via capillary action to fluid stop B, preferably a capillary stop, forming a metered sample within a sample metering chamber between point D and fluid stop B. The second pouch is then ruptured causing fluid, e.g., diluent, contained therein to flow to a fluid stop D, which also preferably is a capillary stop. A metered amount of the fluid, e.g., diluent, situated between pump opening C and point D may then be transferred by a second pump into the sample metering chamber where it simultaneously mixes with the metered sample and transfers the resulting diluted/mixed sample past fluid stop B and into the analysis conduit for assay formation and analysis. FIG. 2H also includes a first fluid pouch and associated pump for an additional fluid, e.g., wash fluid or reactant. Of course, this embodiment could include a third pouch and associated pump for incorporating a third fluid, as described above.

Figure 2I:
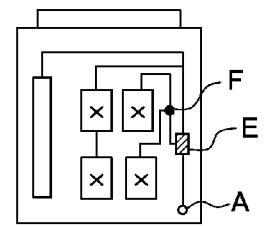

FIG. 2I illustrates an embodiment that is suited for high range sample dilution or sample mixing, similar to the embodiment in FIG. 1, but including only two fluid pouches and associated pumps. In this embodiment, sample flows into a sample extraction unit E, and a second fluid from the second pouch, optionally a diluent, which may or may not be metered, is pumped by the second pump through and/or over a portion of the sample extraction unit. A metered diluent may be formed, for example, in a diluent conduit between point F, which receives air from the associated pump into the diluent conduit, and the sample extraction unit E. This causes a small portion of the sample to be extracted into the second fluid, e.g., diluent, forming a high range dilution/mixed sample that is then pumped with the second pump to the analysis conduit for assay formation and analysis. Fluid, e.g., wash fluid or reactant, from a first pouch also may be pumped, preferably independently from the sample and second fluid, to the analysis conduit.

In another embodiment, the invention is to a process for using any of the aforementioned multi-fluidic cartridges. For example, in one embodiment, the invention is to a process for analyzing a fluid sample with a multi-fluidic cartridge, comprising: (a) introducing the fluid sample into a sample entry port and allowing the fluid sample to enter a first conduit beginning at the sample entry port and in fluid communication with one or more sensors; (b) rupturing a plurality of fluidic pouches, each containing a different fluid and in fluid communication with a respective delivery conduit configured for delivering the respective fluid to the first conduit; (c) transporting the different fluids through the delivery conduits and to the first conduit; (d) transporting the fluid sample through the first conduit and over the one or more sensors; and (e) analyzing the fluid sample at the one or more sensors for the presence or concentration of an analyte or a property of the fluid sample. The process optionally comprises a step of mixing at least one of the different fluids with the fluid sample in the first conduit. Preferably, at least two of the delivery conduits are in fluid communication with a shared conduit, and the process further comprises the step of transporting a plurality of the different fluids from at least two of the delivery conduits through the shared conduit, separately or together, and to the first conduit.

In this process, the transporting of the different fluids to the first conduit may occur before, after, or both before and after the transporting of the fluid sample through the first conduit and over the one or more sensors. For example, in one embodiment, at least one of the different fluids is transported to the first conduit before step (d), and at least one of the different fluids is transported to the first conduit after step (d). In one aspect of this embodiment, for example, it may be desirable to transport, i.e., deliver, a diluent to the first conduit before step (d) so that it may mix with the sample prior to sample analysis, and then transport the resulting diluted sample to the one or more sensors in step (d), followed by transporting a second fluid, such as a wash fluid, after step (d) to the one or more sensors.

Multi-Fluidic Cartridge Readers

The above-described multi-fluidic cartridges preferably are used in combination with a reader or reading device. Typically, a sample such as blood is introduced into a cartridge as described above and the cartridge is inserted into the reader. Preferably, the reader is suitable for reading various types of cartridges with different tests or combinations of tests. The user may identify the type of cartridge being used such that the reader can select, e.g., from a look up table, the proper test parameters, e.g., fluid rupturing, pumping and sample flow sequence, for the selected cartridge.

Point-of-care blood analysis systems are generally based on a re-usable reading apparatus that performs blood tests such as, but not limited to, analyte detection, electrolyte detection, blood gas detection, coagulation testing, hematology, and testing for glucose and cardiac markers. In preferred embodiments, the point of care blood analysis systems of the invention perform tests, e.g., blood tests, using a disposable cartridge that contains: (i) analytical elements, such as microfabricated biosensors, e.g., electrodes for sensing analytes such as pH, oxygen and glucose; (ii) fluidic elements, e.g., conduits for receiving and delivering the blood sample to the electrodes; and (iii) calibration elements, e.g., aqueous fluids for standardizing the electrodes with a known concentration of each analyte. The readers contain the electronics and algorithms for operating the electrodes, e.g., making the measurements and performing computations. The readers preferably also have the ability to display results and communicate those results to the laboratory and hospital information systems (LIS, HIS) optionally via a computer workstation. Communication between the reader and a workstation may be via various means such as via an infrared link or between a workstation and a laboratory information system using a hard wire connection or other similar means. Those skilled in the electronics and communications arts will recognize that other data transmission means can be employed, e.g., various wireless protocols.

Several technologies within the general areas of sensing electrodes, measurement methods, single-use cartridges and readers (also referred to as analyzers and instruments) are disclosed in the following jointly owned patents: U.S. Pat. No. 5,112,455; U.S. Pat. No. 5,096,669; U.S. Pat. No. 5,212,050; U.S. Pat. No. 5,200,051; U.S. Pat. No. 5,447,440; and U.S. Pat. No. 7,419,821, each of which is incorporated herein by reference in its entirety. Further background information is found in the i-STAT® System Manual (Abbott Point of Care Inc., Princeton, N.J.).

While the present invention is mainly described for systems where the physiological sample is blood, plasma or serum, including reagent-amended and diluted forms, it is also applicable to the analysis of other biological materials such as, but not limited to, urine, saliva, vaginal, fecal, bronchial and gastric secretions. The disposable diagnostic devices can include, for example, urine analysis devices, saliva analysis devices, and cheek swab analysis devices.

As indicated above, the invention also may be applied to other analytical systems known in the art, where a single-use testing device or cartridge has a sensing means. Such systems may include, for example, systems based on electrochemical principles, e.g., potentiometry, amperometry and conductimetry, and testing systems typically referred to as electrodes, modified electrodes, ion-selective electrodes, enzyme electrodes, immuno-electrodes, strip electrodes, biosensors, immunosensors and the like. Also included are systems that are based on optical methods, for example, detecting turbidity, or absorbance at one or more selected wavelength, evanescence, fluorescence, luminescence, wave guides, reflectance and the like. These devices can use similar fluidics to the i-STAT® System, at least to the extent that a test sample is delivered to a testing region in each device, and that the devices are operated with a reading apparatus. Thus, the present invention is also applicable to these systems, primarily but not exclusively, where these systems are used at the point of patient care, e.g., the operating room, emergency room or physician's office.

In an exemplary embodiment, the reader is generally hand-held, portable or having a small bench-top footprint. It is preferably free-standing and battery operated so that it can be easily moved to a bedside location if desired. However, it may be attached to main power or intermittently to a battery re-charger attached to main power.

One of the main values of point of care blood testing systems is that the time-consuming need to send a patient's blood sample to a central laboratory for testing is eliminated. These systems are sufficiently easy to operate that a technician or nurse, at the bedside, can obtain a reliable quantitative analytical result, equivalent in quality to the laboratory. In a preferred embodiment, the technician selects a cartridge with the required panel of tests, draws a blood sample, dispenses it into the cartridge, seals the cartridge and inserts the cartridge into the reading device. The reading device then performs a test cycle that includes the necessary analytical steps to successfully generate a test result. Such simplicity gives the user speedy insight into a patient's physiological status. In addition, by reducing the time for evaluation, it enables a quicker decision by the physician on the appropriate treatment, thus enhancing the likelihood of a successful patient outcome.

In the emergency room and other acute care locations within a hospital, the types of blood tests required for individual patients tend to vary. Thus, point of care systems generally offer a range of disposable cartridges with different menus of blood tests. In addition to tests for sodium, potassium, chloride, calcium, bicarbonate, partial pressure of oxygen ($pO_2$), partial pressure of carbon dioxide ($pCO_2$), pH, glucose, hematocrit, hemoglobin, ammonium, lactate, blood urea nitrogen (BUN) and creatinine, others can include prothrombin time (PT), PT/INR, activated clotting time (ACT), activated partial thromboplastin time (APTT), hemoglobin $A_1C$, heparin anti-$X_a$, blood culture, troponin I, troponin T, creatine kinase MB (CKMB), brain natriuretic peptide (BNP), NTproBNP and C-reactive protein (CRP). As is well known in the art, several other parameters can be calculated from these test results, including for example base excess (BE), anion gap, and percentage of oxygen saturation (% $O_2$ sat). These tests can be provided in several combinations to the user in a single-use device, e.g., disposable cartridge. For example, the i-STAT® system offers hospitals more than ten types of cartridges with menus that range from one to eight or more blood tests. These test menus are configured so that each test is compatible with a given anticoagulant, and the manufacturer specifies the given anticoagulant or anticoagulant options in the product literature. Conventionally, where tests require different anticoagulants, they are provided in separate cartridges. For example, a 3.2% citrate concentration is preferred for coagulation testing.

As a result, a given facility, e.g., a hospital, may use multiple types of cartridges. FIG. 21 illustrates a number of exemplary cartridges for use with the i-STAT® system, including a cartridge for "core" testing for electrolytes and chemistries, coagulation testing, immunoassays, and the like. FIG. 21 also illustrates an "x" denoting each actuation point on the respective cartridges for triggering testing steps by the handheld testing apparatus. Thus, the testing apparatus includes a mechanical assembly for applying force to the actuation points at appropriate times to perform the respective tests associated with each cartridge. For example, the sample may be diluted with water or buffer, or be amended by adding reagent, e.g., enzyme, dyes, antibodies, enzyme cofactors and substrates and the like. For conventional i-STAT cartridges, two actuation points along a primary cartridge axis are included. Thus, a corresponding testing apparatus requires only a singular mechanism that is aligned with this axis for actuating these two actuation points, with movement of either the cartridge or the mechanism along the straight line for access to the other of the two actuation points. While this design is highly desirable for simplicity of operation, it is somewhat limiting in terms of the functional ability of a given cartridge due to the limited number of contact points.

With the creation of the novel multi-fluidic cartridges described above, increasingly advanced testing advantageously may be achieved, creating the need for readers capable of manipulating such cartridges in a desired manner. The novel readers of the invention have an increased ability for controlling and/or actuating the respective features of these multi-fluidic cartridges. For example, the reader may perform appropriate fluid mixing and/or channeling in accordance with the desired testing procedure. As shown in FIG. 2A, described above, the testing cartridge may include chambers and corresponding actuation points aligned in rows of three. For such cartridges, there is a need for an apparatus, e.g., reader, having augmented mechanisms for triggering the additional actuation points on either side of the center actuation points corresponding to the legacy cartridges illustrated in FIG. 21. Since conventional readers are not configured for use with the multi-fluidic cartridges of the invention, the need exists for a way to modify existing readers (so-called "legacy readers") so that they may be able to manipulate such cartridges. In some embodiments, a conventional legacy readers may be retrofitted or modified for use with the novel multi-fluidic cartridges of the invention. The need also exists for entirely new reader configurations that are suited for use with the novel multi-fluidic cartridges of the invention.

A. Single Motor Control of External Plungers

Figure 3A:
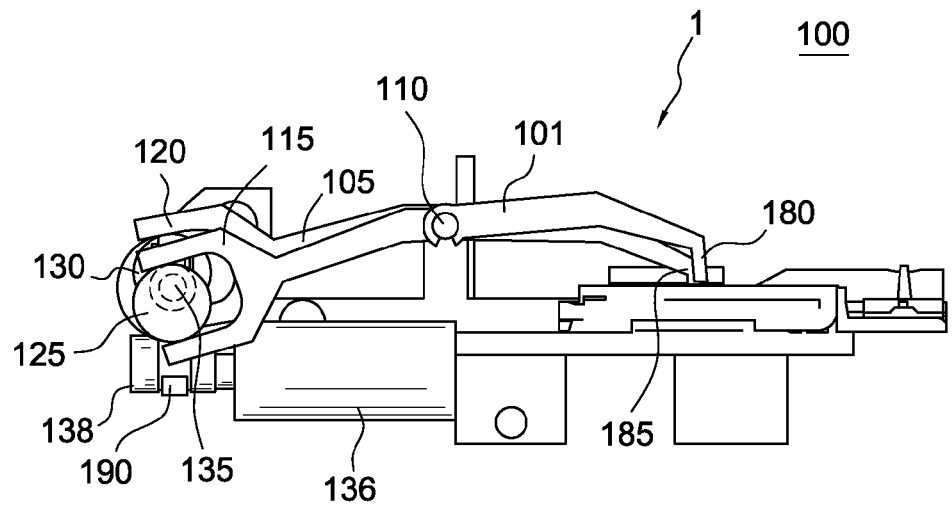
FIG. 3A illustrates a side view of a multi-fluid cartridge reader device for fluidic analysis according to a preferred embodiment of the present invention, excluding components for legacy functions (e.g., sample plunger, calibrant plunger and 18 pin connector)
Figure 3B:
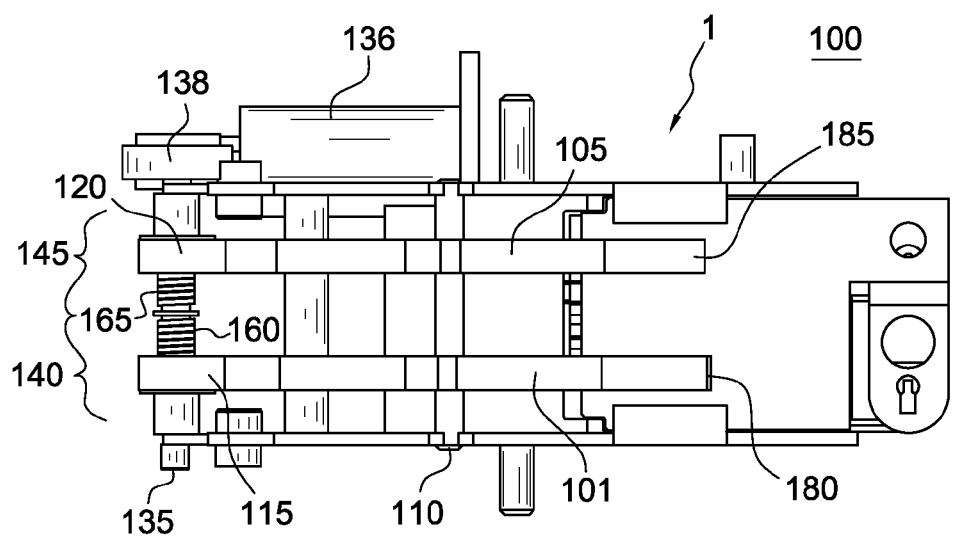
FIG. 3B illustrates a top view of the device of FIG. 3A.
Figure 3C:
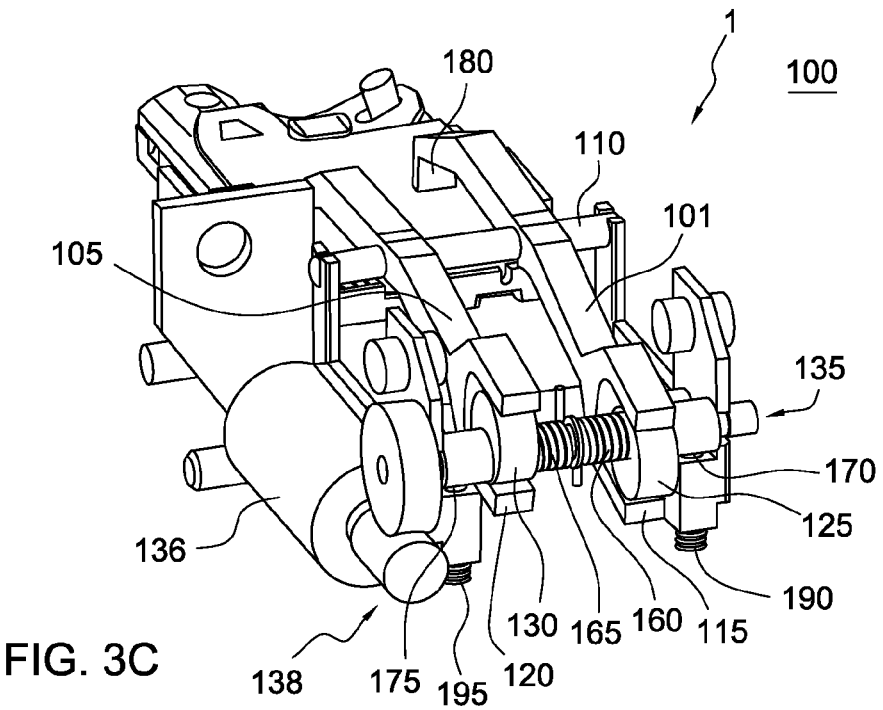
FIG. 3C illustrates a rear perspective view of the device of FIG. 3A.
Figure 4:
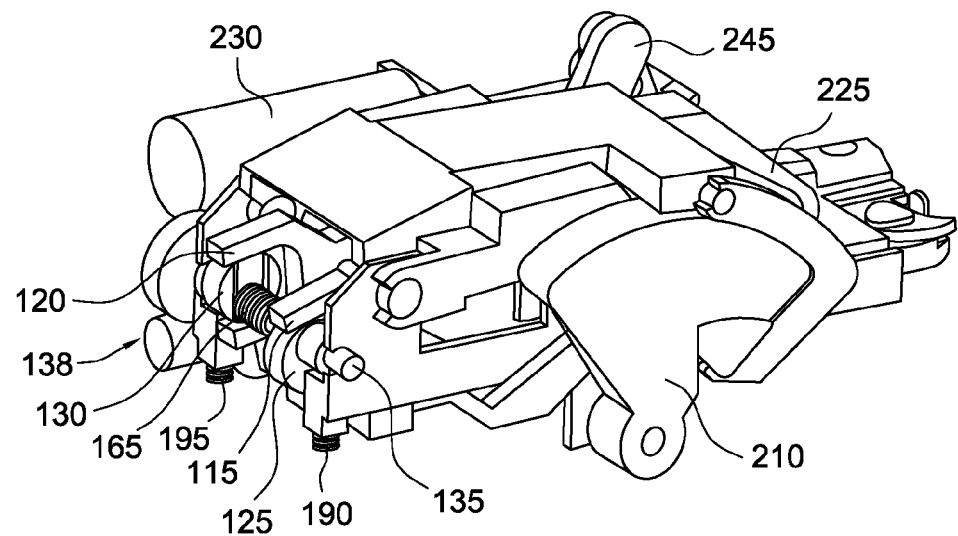
FIG. 4 illustrates a side perspective view of the device of FIG. 3A.
Figure 5A:
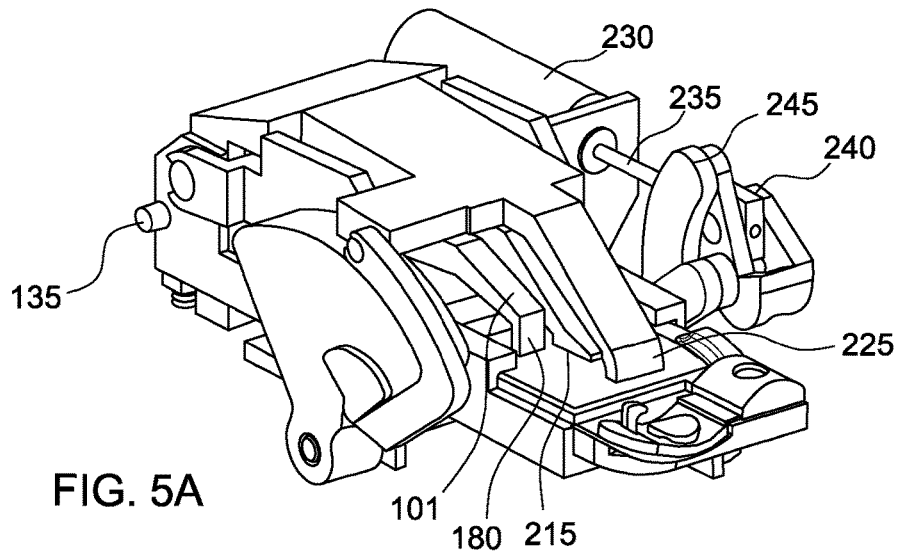
FIG. 5A illustrates a front perspective view of the device of FIG. 3A while in a "down" position.
Figure 5B:
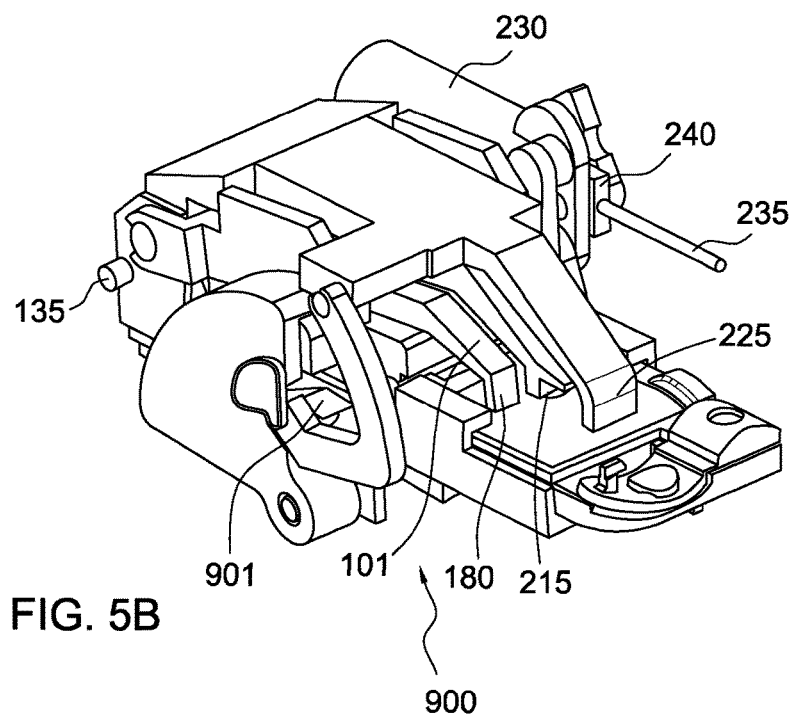
FIG. 5B illustrates a front perspective view of the device of FIG. 3A while in an "up" position.

In a first reader embodiment, a single motor is used to control movement of multiple plungers, e.g., the outside plungers of the reader as shown in FIGS. 3-5. FIGS. 3A, 3B, and 3C respectively illustrate a side view, a top view, and a perspective view of an exemplary multiple plunger pouch-actuation mechanism 1 in a multi-fluidic cartridge reader 100 according to one embodiment of the invention. FIG. 3A presents a side view of plungers 101 and 105 for actuating and rupturing multiple pouches of a multi-fluidic cartridge (shown on the right side of the reader immediately under plungers 101 and 105) for fluidic analysis according to one embodiment of the invention. For clarity, FIGS. 3A-3C do not show the central plunger associated with the legacy readers. The outside plungers 101 and 105 pivot in the middle region thereof about a common pivot shaft 110 that is disposed over an 18-pin connector (not shown). Each plunger 101 and 105 is driven at the back-end by a yoke 115 and 120 that captures an eccentric cam 125 and 130, respectively. The two plungers 101 and 105 straddle a third (central) plunger 215 (shown in FIGS. 5A and 5B), also referred to as a calibrant plunger or a pushpin. In this manner, the fluid pouches contained in the multi-fluidic cartridges may be positioned up to three abreast.

Referring to FIG. 3B, the eccentric cams 125 and 130 share one common camshaft 135. The eccentric cams 125 and 130 turn freely on camshaft 135, which preferably is driven by a dedicated DC motor 136, which may be a DC coreless brush-type gear-motor, via a worm-gear and worm combination 138.

Each eccentric cam 125 and 130 has a relative-motion-actuated wrap spring clutch mechanism 140 and 145 that engages the cam 125 or 130 and locks it to the shaft 135 when the shaft 135 turns in a particular direction corresponding to the eccentric cam 125 or 130. In this embodiment, the wrap spring clutch mechanism 140 or 145 preferably slips (i.e., the cams 125 and 130 do not move with the shaft 135) when the camshaft 135 turns in the opposite direction corresponding to the other eccentric cam 130 or 125.

The wrap spring clutch mechanisms 140 and 145 are configured so that one cam 125 or 130 moves when the shaft 135 turns clockwise, and the other cam 130 or 125 moves when the shaft 135 turns counterclockwise. Each clutch mechanism 140 and 145 has a slot 405 and 415 (see FIG. 6) on the side that engages a free end of a wrap spring 160 and 165, thereby causing the corresponding spring 160 or 165 to tighten or release its grip on the camshaft 135 with slight relative motion between the cam 125 or 130 and the camshaft 135. Correspondingly, passive drag brakes (spring loaded pads) 170 and 175 against cams 125 and 130 provide friction for springs to release with "counter-lay" rotation. Thus, motor direction determines which of cams 125 and 130 operates (i.e., moves with the shaft), and therefore cams 125 and 130 move in opposite directions, each moving in one direction only. As a result, the respective plungers 101 and 105 are moved separately depending on the direction of rotation of gear-motor 136 via clutch mechanisms 140 and 145 and cams 125 and 130, enabling separate control of plungers 101 and 105 to compress corresponding fluidic pouches aligned to tips 180 and 185 thereof by controlling the direction of a single gear-motor 136. One or more microprocessors, or electronic or mechanical controllers, may be used to provide direct or programmable control over gear-motor 136.

As shown, for cams 125 and 130, one half of a revolution of camshaft 135 in their respective corresponding direction translates to full displacement although other configurations may be possible. In the embodiment shown, a full revolution results in a reset from home position to home position of the assembly. Cams 125 and 130 and yokes 115 and 120 can be moved in any order, intermittently or continuously, up to a fixed maximum displacement through controlling gear-motor 136. The device may further include a camshaft relative position encoder (not shown) and yoke home position detectors (not shown) for monitoring and refining control of the above-described mechanism for driving plungers 101 and 105.

The fluid pack plungers 101 and 105 may move in a sinusoidal pattern, each plunger 101 and 105 having a fixed amplitude. Optionally, plungers 101 and 105 may be configured to have different amplitudes from one another by varying cam eccentricity and/or varying position of the plunger fulcrum along the length of the plunger. The plungers 101 and 105 can be stopped and/or driven intermittently. Preferably, the direction of the plungers may not be reversed, and hence, they are returned to their respective home positions by completing their respective forward periodic motions. In one embodiment, the plungers 101 and 105 oscillate by continuous forward motion. The oscillation speed depends on the gear-motor speed, which may be controlled by varying applied voltage, changing the reduction ratio of the motor gearhead, or changing gear-motor speed-load characteristics (e.g., armature design, etc.).

Referring to FIG. 3C, a rear perspective view of the gear-motor 136 and gears 138 is shown. The set-screws 190 and 195 on the bottom of the assembly serve as adjustable drag brakes preferably acting to preload springs (not shown) that push pads 170 and 175 against each cam 125 and 130, respectively. Each brake preferably provides enough friction to hold the cam 125 and 130 so that the camshaft 135 develops "release torque" to disengage the wrap spring 160 and 165. The amount of brake holding force depends upon the brake adjustment; however, a higher holding force may tend to create parasitic drag. The brake may also hold the cam in the event release torque due to residual contact force between the yoke and cam during "falling" segment of the cam movement, i.e., when torque on the cam due to plunger load changes sign.

Figure 6:
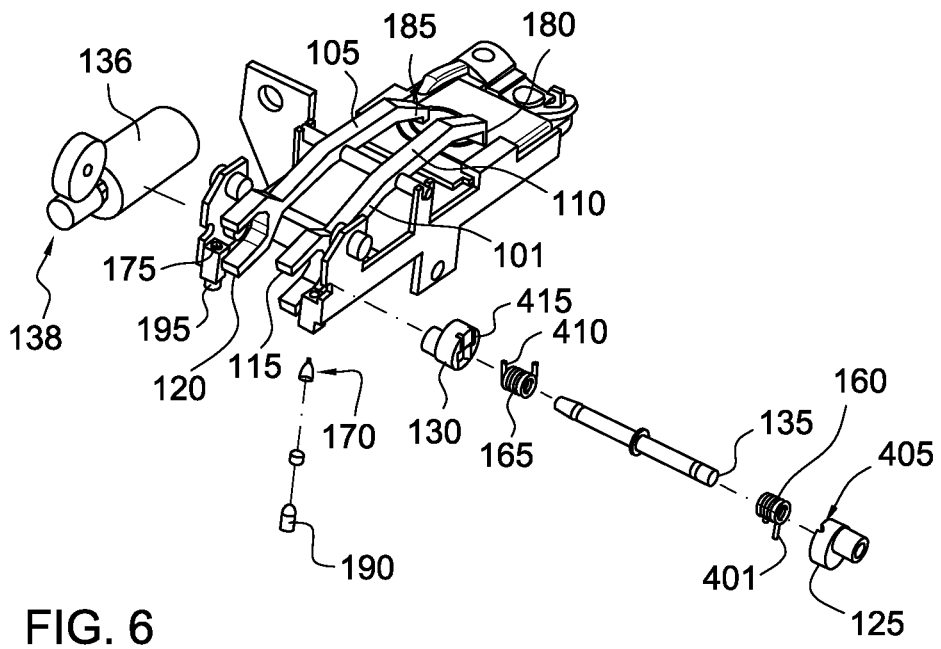
FIG. 6 illustrates an exploded view of the plunger actuation portions of the device of FIG. 3A.

FIG. 6 provides an exploded view of plungers 101 and 105. Right spring 160 has an arm 401 captured in a slot 405 in right cam 125. Similarly, left spring 165 has arm 410 captured in a slot 415 in left cam 130. In this manner, springs 160 and 165 are effectively attached, at their outer ends, to cams 125 and 130, respectively. The spring coils of springs 160 and 165 preferably have a slight interference with shaft 135. Springs 160 and 165 may or may not slip on shaft 135, depending on direction of rotation of shaft 135.

As shaft 135 rotates clockwise (viewed from right), friction between shaft 135 and right spring 160 causes the spring coils thereof to wind more tightly against shaft 135, causing spring 160 and right cam 125 to move with the shaft against friction of the brake 170. Simultaneously, friction between shaft 135 and left spring 165 causes the spring coils in left spring 165 to unwind slightly, loosening the grip on shaft 135 and allowing shaft 135 to rotate while spring 165 and left cam 130 remain stationary. The spring 165, thus, holds some potential energy due to being expanded slightly over the shaft 135. This preload determines the amount of torsion that must be applied to the spring to get it to begin unwinding.

Thus, in the slip direction (as shown, clockwise for spring 165 and cam 130 and counterclockwise for spring 160 and cam 125) as shaft 135 starts moving, spring 165 or 160 rotates with shaft 135 until the spring arm 401 or 410 contacts the cam 130 or 125 within slot 415 or 405 (preferably at less than 1 degree). Shaft 135 continues to rotate and additional work is put into the spring via torsion and angular displacement to unwind it, starting at the cam-end. Brake 175 lightly holds cam 130, and should hold the cam against this torsional load. If the brake undesirably slips and the cam moves, the spring will not release and the cam will continue to rotate with shaft 135. In some embodiments, it may take a few degrees of shaft movement until the spring has unwound a sufficient amount for the applied torsion to exceed the friction of the remaining coils in order to achieve the slip condition. The amount of spring-shaft interference, spring properties, and surface friction affect the rotation required to slip.

In the no-slip direction, (as shown, clockwise for spring 160 and cam 125 and counterclockwise for spring 165 and cam 130) the spring and shaft should have enough friction to move the cam with very little lag, unless the spring is still holding some incremental strain energy from a previous slip state (the spring is still slightly unwound). If this is the case, it may be necessary to drain that energy before moving the cam.

FIGS. 4 and 5A-5B show various perspective views of the multi-fluidic cartridge reader 100 of FIG. 3, but also showing components for actuating a central pump plunger 225 and a central pouch plunger 215 (preferably a plunger for rupturing a centrally oriented calibrant fluid pouch). The device includes probe assembly 900, which is driven by a sliding follower 901 that follows a cam profile on the interior side of plate cam 210. The central pouch plunger 215, as described above, and the 18-pin connector, also have sliding followers driven by surfaces on plate cam 210. The plate cam 210 is also the input link on a four-bar mechanism 220 that drives a central pump plunger 225. The four-bar mechanism 220 uses pivots instead of sliding cams and therefore has less play (i.e., lost motion/hysteresis).

FIG. 5A provides a front view of the mechanism with the connector and legacy plungers in the "down" position. The legacy motions, for central pouch plunger 215 and central pump plunger 225, preferably are driven by a (second) DC motor 230. A gearmotor 230 drives a linear lead screw 235, which drives a straight-line mechanism 240 (Chebyshev shown). Output of the straight-line mechanism 240 is rotation of "banana" link 245. The banana link 245 turns a shaft (not shown) that passes under the mechanism and drives the plate cam 210. The straight-line mechanism affords transformation of rectilinear to rotational motion using purely pivoting links which affords no (or minimal) sliding friction or wear, minimal backlash (e.g., no gearing), and no sideloads on the gearmotor output shaft. In another embodiment, the straight-line mechanism 240 may be replaced with a rotating control horn. Such embodiment may have the linear translating nut of the leadscrew captured in a slot on a pivoting control horn that in turn rotates a shaft that causes the plate cam to rotate. A third embodiment may have the linear translating nut of the leadscrew pinned to a coupler link that terminates with a pinned joint on the pivoting control horn—eliminating the sliding action.

FIG. 5B illustrates the front view of the mechanism in reader 100 in an "up" position where motor 230 has driven the mechanism and plungers 215 and 225 to the up position via straight-line mechanism 240.

In additional embodiments, not shown, the three element (e.g., plunger) mechanism described above may be "doubled up" as desired in order to provide six independent actuations. Of course, additional clutches and independent motors may be employed to derivative mechanisms of those disclosed to get four, five, six or more actuators. Alternatively, the reader may include a drive system to move the cartridge back and forth in a longitudinal direction (further into and out of the reader) so as to actuate multiple actuation points along multiple (e.g., two or three) longitudinally extending lines. For example, one or more pouches may be initially ruptured by a first actuation motion, followed by a step of moving the cartridge longitudinally further into the reader with the drive system, followed by additional actuation steps to actuate one or more pumps, preferably in a predetermined and preprogrammed order, in order to cause the fluid contained in the various pouches to fluidically move throughout the cartridge as desired.

B. Independent Motor Control

Figure 7:
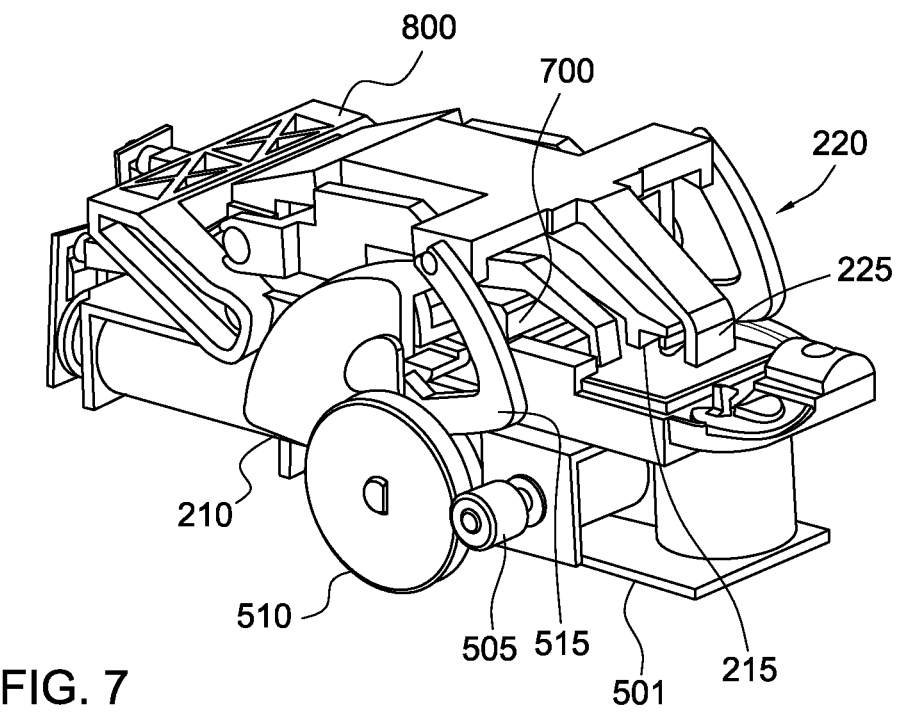
FIG. 7 illustrates a side perspective view of a multi-fluid cartridge device for fluidic analysis according to a second preferred embodiment of the present invention.

In another embodiment of the invention, multiple direct drive motors may be used to independently control the various pouch and pump actuation mechanisms of the multi-fluidic cartridges of the invention. FIGS. 7-20 illustrate an exemplary reader according to this embodiment of the invention. FIG. 7 provides a perspective view of an apparatus 500 incorporating multiple direct drive motors that independently drive the plungers. This exemplary embodiment incorporates certain features that correspond to those of the above-described embodiment using eccentric cams on a common camshaft. Thus, such features will be referred to using the same reference numerals, and detailed description thereof will not be repeated hereafter.

The view shown in FIG. 7 illustrates a transverse (e.g., 12 mm diameter) hollow-core DC motor 501 under the apparatus with a high reduction gearhead preferably from 3000:1 to 4000:1 driving a pinion 505 that engages a spur gear 510 forming a 4:1 spur-gear reduction. Other ratios may be suitable for transforming the speed-load characteristics of the selected gearmotor, to the speed-load-displacement requirements of the apparatus. The plate cam 210 drives followers to move various motion "outputs" including: (1) the central pouch plunger 215 (also referred to as a push pin or calibration pack plunger), (2) the 18 pin connector 700, and (3) a thermal probe 800. The plate cam 210 is also the input link for a 4-bar mechanism 220 that drives another output, (4) the central pump plunger 225 through a coupler-link 515, shown as the "elbow" shaped link behind the large spur gear.

The embodiment described above may have only one plate cam 210 providing input to the described motion outputs of the apparatus. A single plate cam input suggests the described outputs are driven by asymmetrical loads or reactions on the sliding follower joints that engage the off-centerline plate cam. The outputs may have sufficient structural stiffness to function under the affect of side loading. Alternatively, a second, or "mirrored," plate cam 1001 (see FIG. 12) may be envisioned on the opposite side of the apparatus, coupled to the first plate cam by a cross shaft that passes under the apparatus. The mirrored cam would drive the same output motions via redundant joints of the same types (followers and pivot) on the opposite side of the apparatus. In this embodiment, a coupled pair of plate-cam inputs may load the outputs (central pouch plunger, 18 pin connector, thermal probe and central pump plunger) symmetrically, reducing or eliminating torsional deflection in these structures. Practioners skilled in the art will recognize the cross-shaft coupling between the plate cams will experience torsional strain, potentially causing differential and load dependent movement of the plate cams, affecting the symmetry of loading on the outputs. Differential displacement of the plate cams may be compensated for by refinement of the individual plate cam profiles (i.e., not exact mirrored copies) to further improve symmetry of loading on the outputs.

Figure 8:
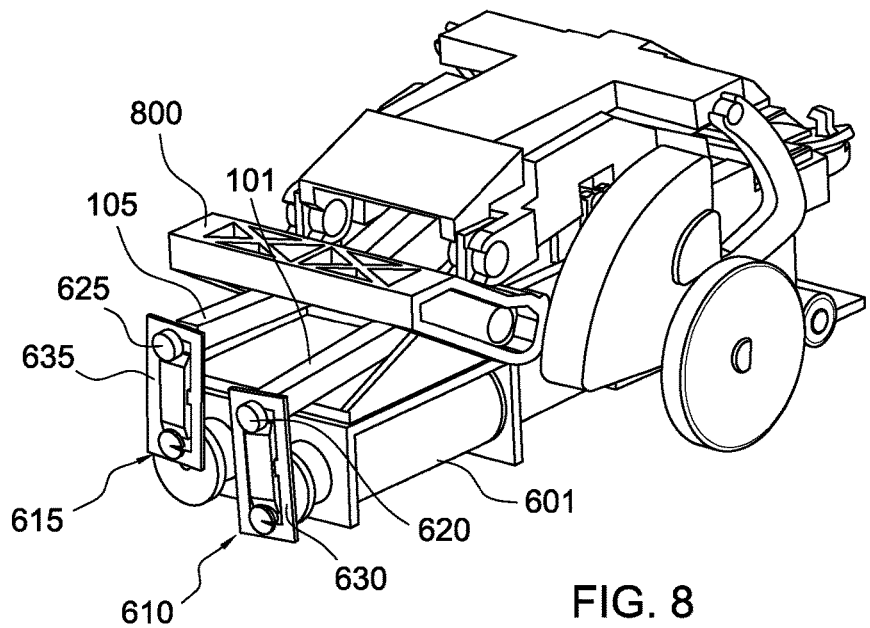
FIG. 8 illustrates a front perspective view of the device of FIG. 7.
Figure 9:
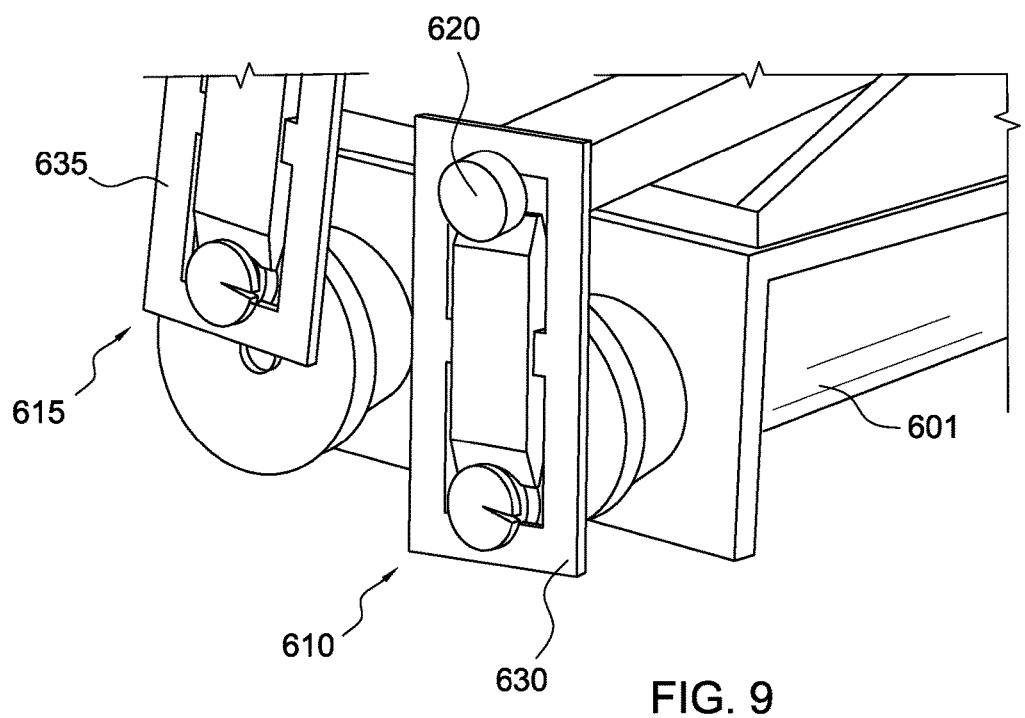
FIG. 9 illustrates a detail view of the pivots attached to the ends of the plungers of the device of FIG. 7.
Figure 10:
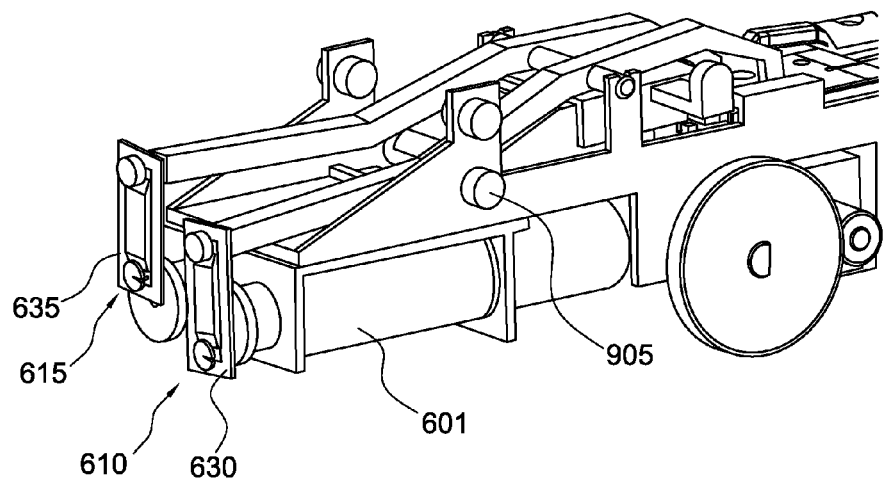
FIG. 10 illustrates a pivot between the 18-pin connector and a plunger of the device of FIG. 7.
Figure 12:
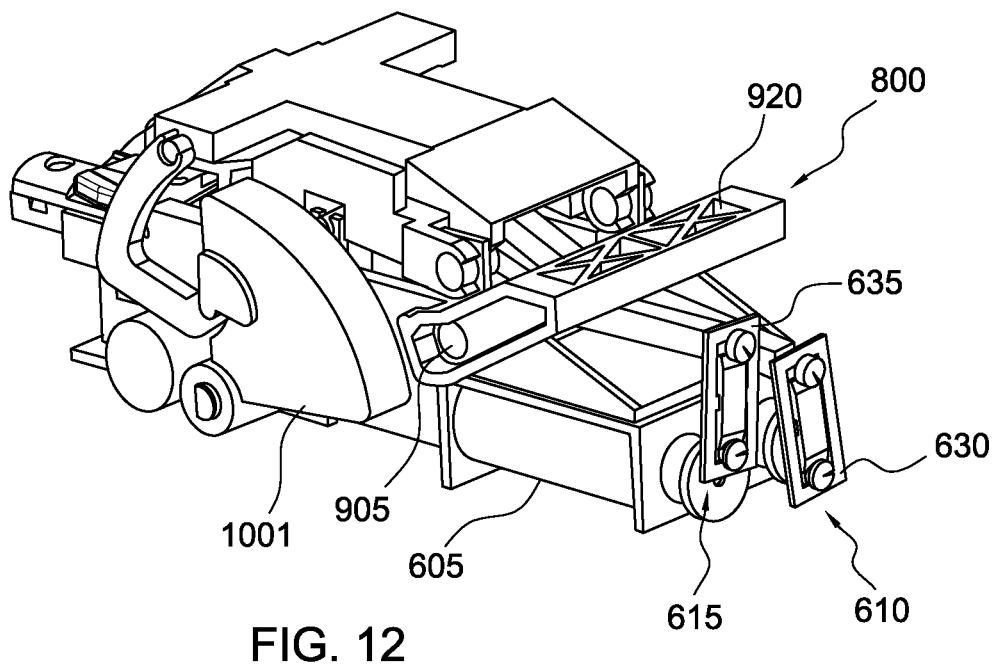
FIG. 12 illustrates a mirrored cam portion of the device of FIG. 7.

FIGS. 8 and 12 show "double barreled" gearmotors 601 and 605, respectively, the ends of which drive the fluid pack plungers 101 and 105 using spatial (non-planar) 4-bar mechanisms. The side-by-side gearmotors 601 and 605 (see FIG. 12) constitute ground links, independently driving crank-type input links comprised of eccentric pivots 610 and 615, located on flanged couplers, mounted directly to the output shafts of the gearmotors. As shown in FIG. 8 and FIG. 9, the eccentric crank pivots 610 and 615 are attached to the ends of coupler links 630 and 635. The opposite ends of coupler links 630 and 635 attach to the ends 620 and 625 of the plungers 101 and 105 (i.e., output links). Note the plungers 101 and 105 reside in planes perpendicular to the plane of the crank inputs, hence producing non-planar 4-bar kinematics. To accommodate the 3D kinematics of the spatial links without complex miniature ball joints, each end of the coupler links (snap couplers 630 and 635) attach to the aforementioned links with "saddle" shaped "knife edges" that snap into corresponding tapered, radiused grooves on the plungers and eccentric pivots. The saddle geometry accommodates planar and out-of-plane movement, and reduces Hertzian contact stress. The length of the plungers 101 and 105 reduces the side loading on gearmotors 601 and 605 to an acceptable level.

Figure 11:
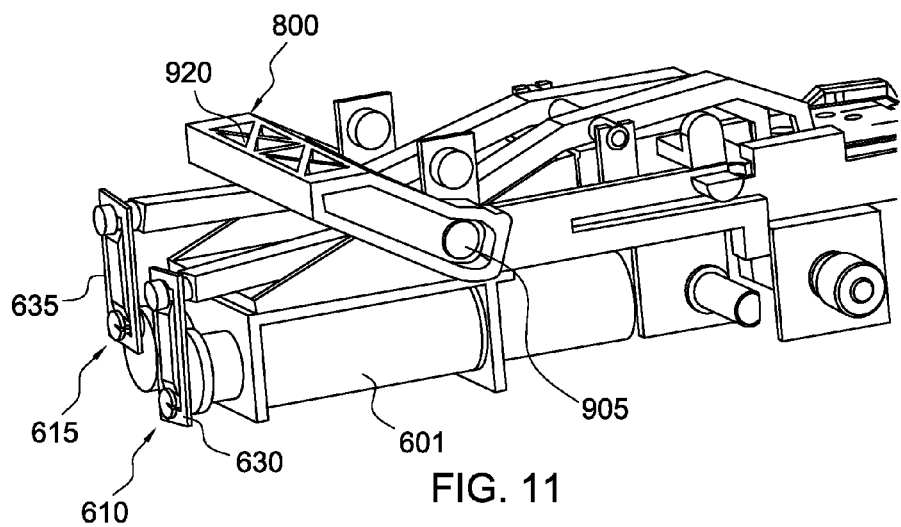
FIG. 11 illustrates a thermal probe portion of the device of FIG. 7.

FIG. 11 illustrates a thermal probe 900 and a guiding boss fixed to ground 905. The overall "tuning fork" shape of the thermal probe creates structural flexibility between the follower on the top arm, which follows a cam profile prescribed by the plate cam 210 (not shown), and the thermal probe towers held by the lower arm underneath the apparatus, which are brought into contact with the cartridge with sufficient force to minimize thermal contact resistance for temperature measurement and establish electrical connection to heat the cartridge. The structural flexibility of the shape may be tuned to allow the follower to kinematically over-travel, compensating for dimensional variability (i.e., tolerances) without need for mechanical adjustment, and allow the towers to contact with required force by storing strain energy in the structure, rather than using discrete springs.

As the follower rides along the corresponding profile in the plate cam, the thermal probe assembly follows approximate rotational motion. Bushings at the base of the probe thermal towers translate along guidepins (1220 and 1225 shown in FIG. 14) so that the thermal towers align to a cartridge. In order to compensate for the linear guidepin constraint, the hole around the guiding boss is elongated, allowing the thermal probe assembly to slide on the fixed guiding boss 905. The constant linear velocity along the guidepins at the probe tower base and instantaneous linear velocity along the axis of the elongated hole at the guiding boss result in curvilinear motion of the thermal probe assembly about a non-constant instantaneous center of rotation. Those skilled in the art will recognize in the instance of curvilinear motion that the guiding boss in the elongated hole may be comprised of multiple large-radius arcs (i.e., "American football" shaped rather than round), reducing Hertzian contact stress—and therefore wear—at the joint.

The thermal probe 900 may include a relatively massive cored cross-structure 920 to ensure high torsional stiffness, preferred if there is no mirrored plate cam, to carry asymmetrical loading with minimal deflection that might otherwise adversely affect thermal probe tower contact force. In this aspect, performance, cost and manufacturability of the apparatus will determine the optimal embodiment of mirrored mechanisms (e.g., cams) to implement symmetrical (statically indeterminate) loading, versus stiff structures to minimize torsional deflection with asymmetrical (determinant) loading.

FIG. 12 illustrates the optional mirrored cam 1001 that is mirrored to plate cam 210.

Figure 13:
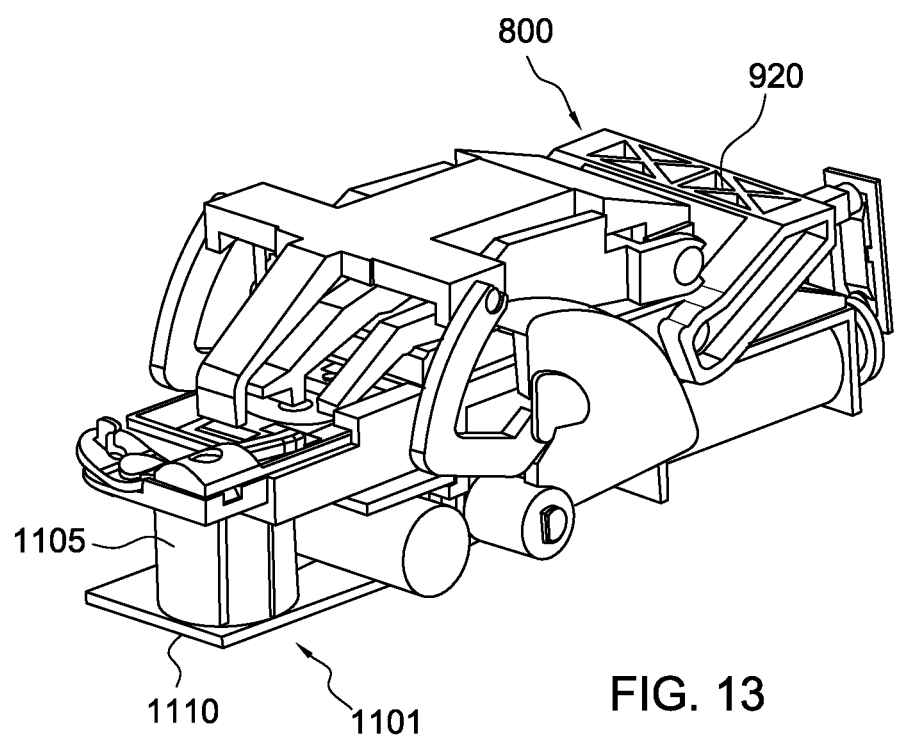
FIG. 13 illustrates a bar code reader assembly portion of the device of FIG. 7.

FIG. 13 is a diagram showing a 2D bar code reader assembly 1101 under the plunger-area of the cartridge. In this aspect, the reader assembly 1101 is represented by a cylindrical shroud 1105 around a digital image sensor (not shown), and an approximately square printed circuit board 1110.

Figure 14:
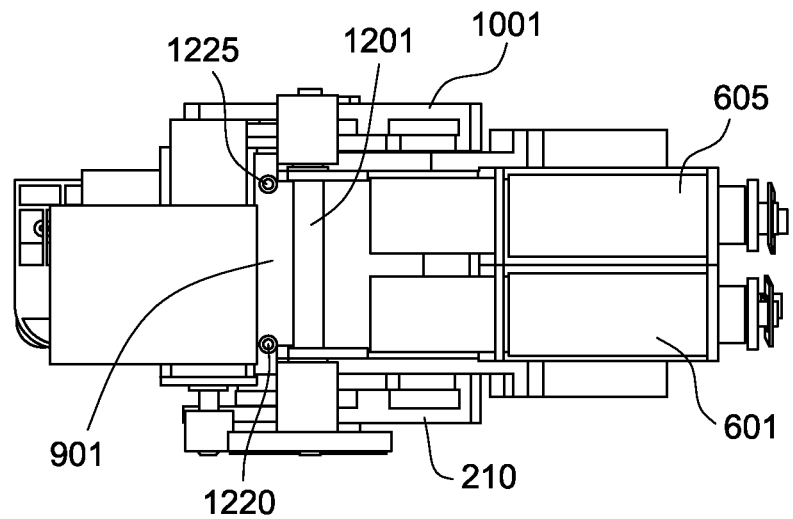
FIG. 14 illustrates a bottom view of the device of FIG. 7.
Figure 15:
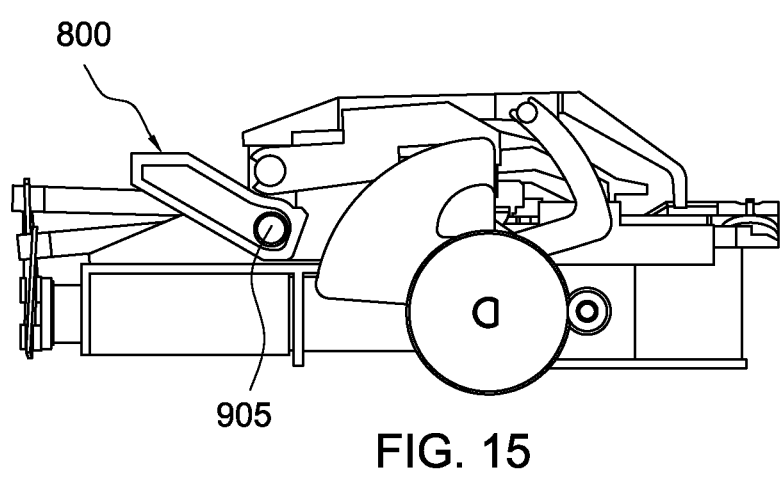
FIG. 15 illustrates a side view of the device of FIG. 7.
Figure 16:
FIG. 16 illustrates a top view of the device of FIG. 7.
Figure 17:
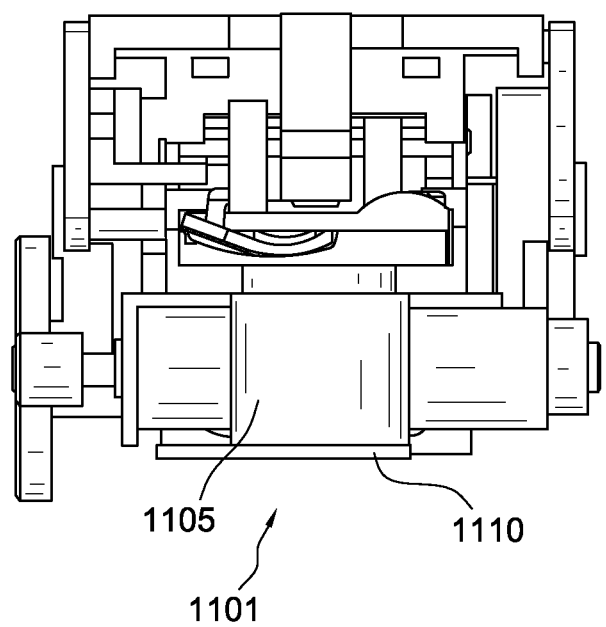
FIG. 17 illustrates a front view of the device of FIG. 7.
Figure 18:
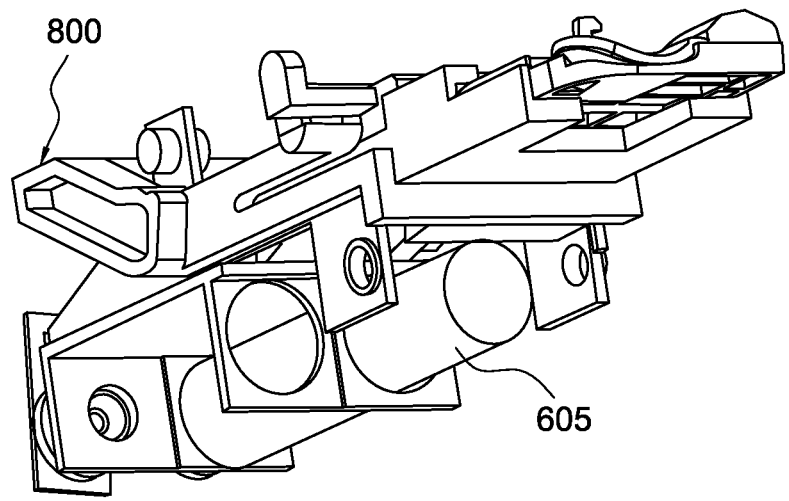
FIG. 18 illustrates a detail view of the thermal probe and motor mounts of the device of FIG. 7.
Figure 19:
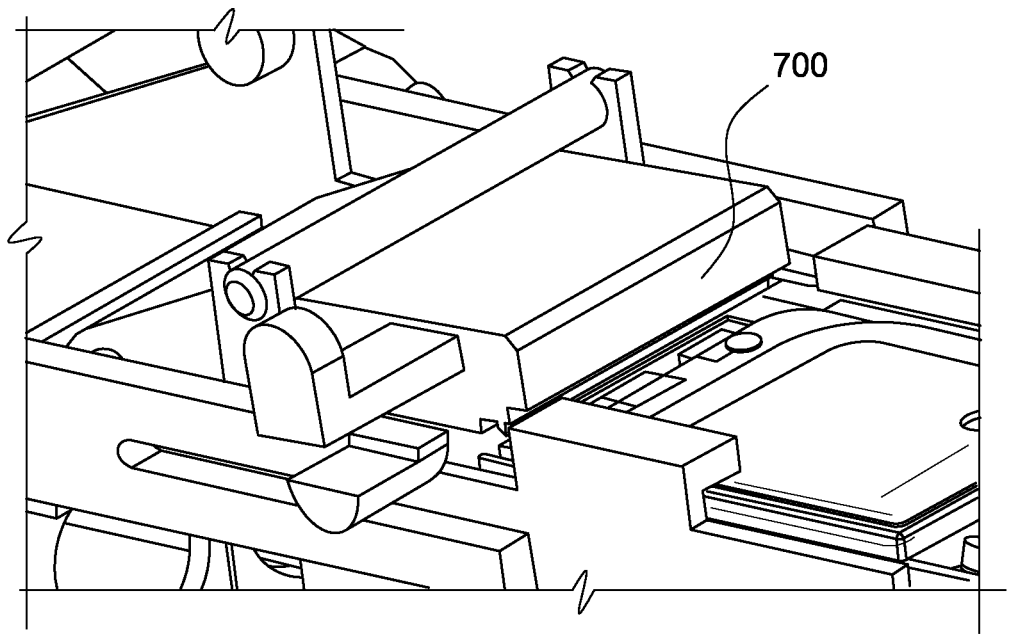
FIG. 19 illustrates a detail view of the pivot and 18-pin connector of the device of FIG. 7.

FIG. 14 provides a bottom view that shows a cross-shaft 1201 coupling the plate cams 210 and 1001. Each gearmotor 601 and 605 is mounted in a plastic holder that secures the motor using the threaded flange on the end of the gearmotor. The motor mount also has a circular governor with clearance fit that contacts and supports the middle of the motor during large side impact. FIG. 14 further illustrates guidepins 1220 and 1225 in the probe base for aligning thermal probe 800 to a cartridge, as described above. FIGS. 15-18 illustrate additional views of the above-described reader device, and FIG. 19 illustrates a detail view of the pivot and 18-pin connector of the reader device.

Figure 20:
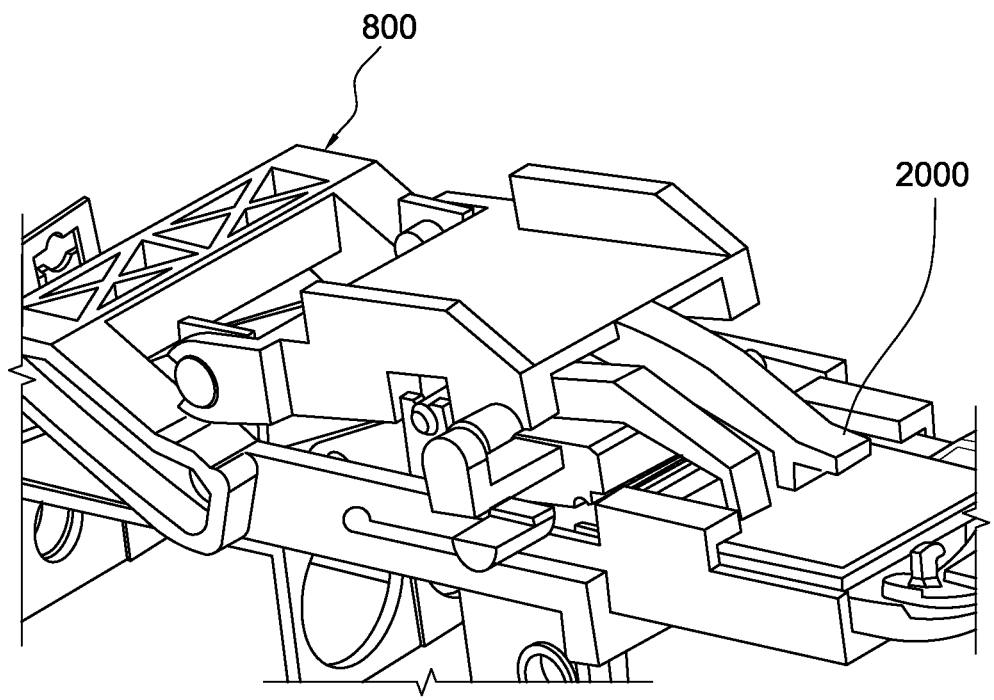
FIG. 20 illustrates a detail view of one of the plungers of the device of FIG. 7.

FIG. 20 illustrates details of the cal-plunger. Note the follower nested behind the follower for the 18 pin connector. The followers are sliding, non-circular to reduce Hertzian contact stress. The three followers follow different surfaces on the plate cam. The "nose" 2000 sticking out the front of the cal plunger is intended to provide "second motion stability," whereby the end of the calibrant pack plunger that contacts the cartridge, displacing small volumes of fluid, is preloaded against the cartridge, reducing movement sensitivity of the calibrant pack plunger (and thereby the fluid) to movement of other parts of the mechanism due to structural coupling. Using the cartridge as a hard-stop for the calibrant pack plunger may eliminate the need for mechanical adjustment to compensate for tolerances. As with the thermal probe, the plunger's driving follower may be designed to over-travel, to compensate for tolerances, and to absorb the resulting strain energy.

The above description provides examples in accordance with the present invention. However, while the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

All United States patents and patent applications, foreign patents and patent applications, and publications discussed above are hereby incorporated by reference herein in their entireties to the same extent as if each individual patent, patent application, or publication was specifically and individually indicated to be incorporated by reference in its entirety.

What is claimed is:

1. A cartridge for sample analysis, comprising:
   (a) a first conduit beginning at a sample entry port for receiving a fluid sample and in fluid communication with one or more sensors;
   (b) a plurality of fluidic pouches, each containing a different fluid and in fluid communication with a respective delivery conduit configured for delivering a respective fluid to said first conduit;
   (c) a plurality of pneumatic pumps configured to move said fluid sample to said one or more sensors and for transporting at least one of said different fluids to said first conduit; and
   (d) a plurality of actuation devices configured to rupture said plurality of fluidic pouches and expel each of said different fluids, wherein one or more of said plurality of actuation devices is a hinged disc.

2. The cartridge of claim 1, wherein each of said different fluids is selected from the group consisting of a reagent fluid, a wash fluid, a calibrant fluid, and a diluent.

3. The cartridge of claim 1, wherein at least two of said delivery conduits are in fluid communication with a shared conduit configured for delivering said different fluids from said at least two of said delivery conduits to said first conduit.

4. The cartridge of claim 3, wherein said shared conduit is in fluid communication with said first conduit at a point downstream of a pump opening.

5. The cartridge of claim 3, wherein out of said plurality of pneumatic pumps, one controls movement of said fluid sample, and at least one controls movement of one or more of said different fluids.

6. The cartridge of claim 5, wherein the pneumatic pump that controls movement of said fluid sample is connected to a pump opening.

7. The cartridge of claim 1, wherein out of said plurality of pneumatic pumps, one controls movement of said fluid sample, and at least one controls movement of one or more of said different fluids.

8. The cartridge of claim 1, wherein movement of each of said different fluids is controlled by a different pneumatic pump.

9. The cartridge of claim 1, wherein said plurality of pneumatic pumps comprises a first pneumatic pump and a second pneumatic pump, wherein said plurality of fluidic pouches comprises a first fluidic pouch and a second fluidic pouch, wherein said first fluidic pouch contains a first fluid and said first pneumatic pump controls movement of said first fluid to said first conduit, and wherein said second fluidic pouch contains a second fluid and said second pneumatic pump controls movement of said second fluid to said first conduit.

10. The cartridge of claim 1, wherein said first conduit includes a pump opening oriented between said sample entry port and said one or more sensors.

11. The cartridge of claim 1, wherein each of said plurality of fluidic pouches is ruptured by a different actuation device.

12. The cartridge of claim 1, wherein each of said plurality of fluidic pouches is oriented within a cavity, and each of said cavities comprises a pin.

13. The cartridge of claim 12, wherein said plurality of actuation devices is configured to rupture said plurality of fluidic pouches in each of said respective cavities on said pin within each of said respective cavities.

14. The cartridge of claim 13, wherein each of said plurality of actuation devices is a hinged disc.

15. The cartridge of claim 14, wherein said hinged discs are configured to flex inwardly into each of said respective cavities upon each of said respective fluidic pouches and cause each of said respective fluidic pouches to rupture on each of said respective pins.

* * * * *